(12) United States Patent
Yano et al.

(10) Patent No.: US 7,253,339 B1
(45) Date of Patent: Aug. 7, 2007

(54) PLANT PHOTOPERIOD SENSITIVITY GENE HD1 AND USE OF THE SAME

(75) Inventors: Masahiro Yano, Tsukuba (JP); Yuichi Katayose, Tsukuba (JP); Takuji Sasaki, Tsukuba (JP); Risa Ishimaru, Tsukuba (JP); Takuichi Fuse, Miyazaki (JP); Motoyuki Ashikari, Nagoya (JP)

(73) Assignees: National Institute of Agrobiological Sciences, Ibaraki (JP); Society for Techno-Innovation of Agriculture, Forestry and Fisheries, Tokyo (JP); National Agriculture and Bio-Oriented Research Organization, Saitama (JP)

( * ) Notice: Subject to any disclaimer, the term of this patent is extended or adjusted under 35 U.S.C. 154(b) by 270 days.

(21) Appl. No.: 10/129,453

(22) PCT Filed: Nov. 1, 2000

(86) PCT No.: PCT/JP00/07693

§ 371 (c)(1),
(2), (4) Date: Apr. 9, 2003

(87) PCT Pub. No.: WO01/32881

PCT Pub. Date: May 10, 2001

(30) Foreign Application Priority Data

Nov. 4, 1999 (JP) .................................. 11/313846

(51) Int. Cl.
*C12N 15/29* (2006.01)
*C12N 15/82* (2006.01)
*C12N 5/04* (2006.01)
*C12N 15/87* (2006.01)
*A01H 5/00* (2006.01)

(52) U.S. Cl. ................... 800/290; 800/298; 800/320.2; 800/278; 536/23.6; 435/320.1; 435/419; 435/410

(58) Field of Classification Search ............... 536/23.1, 536/23.6; 435/320.1, 419, 468, 410; 800/298, 800/278, 290, 320.2
See application file for complete search history.

(56) References Cited

U.S. PATENT DOCUMENTS 5,859,326 A * 1/1999 An ............................. 800/290

FOREIGN PATENT DOCUMENTS

| CA | 2201927 | | 5/1996 |
|---|---|---|---|
| WO | WO 96/14414 | * | 5/1996 |
| WO | WO 01/32880 | | 5/2001 |
| WO | WO 03/100062 A1 | | 12/2003 |

OTHER PUBLICATIONS

MacDonald et al (2003, Cell 113:671-672).*
Kano-Murakami et al (1993, FEBS 334:365-368).*
Bowie et al, Science 247:1306-1310, 1990.*
McConnell et al, Nature 411 (6838):709-713, 2001.*
Fourgoux-Nicol et al (1999, Plant Molecular Biology 40 :857-872).*
Yano M, et al., The Plant Cell, vol. 12, 2473-2483, 2000.*
Ohshima, I. et al., "Linkage analysis of a photoperiod-sensitive gene *Se1* locus with neighboring loci in rice," *International Rice Research Notes*, 21(1):13, Apr. 1996.
Onouchi, H. and Coupland, G., "The Regulation of Flowering Time of Arabidopsis in Response to Daylength," *Journal of Plant Research*, 111(1102):271-275, 1998.
Putterill, J. et al., "The CONSTANS Gene of Arabidopsis Promotes Flowering and Encodes a Protein Showing Similarities to Zinc Finger Transcription Factors," *Cell*, 80:847-857, Mar. 24, 1995.
Robert, L.S. et al., "Conserved structure and function of the Arabidopsis flowering time gene CONSTANS in Brassica napus," *Plant Molecular Biology*, 37(5):763-772, Jul. 1998.
Database EMBL 'Online!, Sep. 23, 1998, Sasaki, T., "*Oryza sativa* (japonica cultivar-group) cDNA for zinc finger protein, complete cds, clone:S12569," *Database accession No. AB001887*, abstract.
Song, J. et al., "Isolation and Mapping of a Family of Putative Zinc-finger Protein cDNAs from Rice," *DNA Research: An International Journal for Rapid Publication of Reports on Genes and Genomes*, 5(2):95-101, Apr. 30, 1988.
Database EMBL 'Online!, Mar. 15, 1999, Wing, R.A. and Dean, R.A., "nbxb0067I06f CUGI Rice BAC Library *Oryza sativa* genomic clone nbxb0067I06f, genomic survey sequence," *Database accession No. AQ396079*, abstract.
Database EMBL 'Online!, Feb. 4, 1999, Wing, R.A. and Dean, R.A., "nbxb0065P05f CUGI Rice BAC Library *Oryza sativa* genomic clone nbxb0065P05f, genomic survey sequence," *Database accession No. AQ366367*, abstract.
Database EMBL 'Online!, Jul. 2, 1999, Wing, R.A. and Dean, R.A., "nbxb0078I18f CUGI Rice BAC Library *Oryza sativa* genomic clone nbxb0078I18f, genomic survey sequence," *Database accession No. AQ688818*, abstract.
Yano, M. et al., "*Hd1*, a Major Photoperiod Sensitivity Quantitative Trait Locus in Rice, Is Closely Related to the *Arabidopsis* Flowering Time Gene *CONSTANS*," *The Plant Cell*, 12:2473-2483, Dec. 2000.
Katayori, Y. et al., "Kouseido Rensa Chizu wo Motoni Shita Shussui ki Kankuosei Idenshi Hd-1 (Se-1) Ryouiki no Butsuri Chizu Sakusei," *Breeding Science*, 46(2):53, 1996.
Yano, M. et al., "Ine Kankousei Idenshiza Hd-1, Hd-2 oyobi Hd-3no Idenshi Hatsuge ni okeru Sougu Sayou," *Breeding Science*, 47(2):224, 1997.
Tsai, K-H., "Studies on Earliness Genes in Rice, with Special Reference to Analysis of Isoalleles as E locus," *Japanese. J. of Genetics*, 52(2):115-128, Apr. 25, 1976.

(Continued)

*Primary Examiner*—Stuart F. Baum
(74) *Attorney, Agent, or Firm*—SEED Intellectual Property Law Group PLLC

(57) ABSTRACT

A rice photosensitivity gene Hd1 is successfully isolated by linkage analysis. It is found out that the photosensitivity of a plant can be modified by transferring this gene or controlling the expression thereof. It is further found out that the photosensitivity of a plant can be evaluated by examining the presence/absence of this functional gene.

10 Claims, 5 Drawing Sheets

OTHER PUBLICATIONS

Altschul, S. et al., "Basic Local Alignment Search Tool," *J. Mol. Biol.*, 215(3):403-410, 1990.

Buzayan, J. et al., "Non-enzymatic Cleavage and Ligation of RNAs Complementary to a Plant Virus Satellite RNA," *Nature*, vol. 323, pp. 349-353, Sep. 1986.

Christou, P. et al., "Production of Transgenic Rice (*Oryza sativa* L.) Plants from Argonomically Important Indica and Japonica Varieties via Electric Discharge Particle Acceleration of Exogenous DNA into Immature Zygotic Embryos," *Bio/Technology*, vol. 9, pp. 957-962, Oct. 1991.

Datta, S.K., "8 Polyethylene-Glycol-Medicated Direct Gene Transfer to Indica Rice Protoplasts and Regeneration of Transgenic Plants," pp. 66-74, 1995.

Dzianott, A. et al., "Derivation of an Infectious Viral RNA by Autolytic Cleavage of in Vitro Transcribed Viral cDNAs," *Proc. Natl. Acad Sci. USA*, 86(13):4823-4827, Jul. 1989.

Ecker, J. et al., "Inhibition of Gene Expression in Plant Cells by Expression of Antisense RNA," *Proc. Natl. Acad. Sci. USA*, vol. 83, pp. 5372-5376, Aug. 1986.

Grosshans, C. et al., "A hammerhead Ribozyme Allows Synthesis of a New Form of the Tetrahymena Ribozyme Homogenous in Length with a 3' end Blocked for Transesterification," *Nucleic Acids Research*, 19(14):3875-3880, 1991.

Hanahan, D., "Studies on Transformation of *Escherichia coli* with Plasmids," *J. Mol. Biol.*, 166(4):557-580, 1983.

Hei, Y. et al., "Efficient Transformation of Rice (*Oryza sativa* L.) Mediated by Agrobacterium and Sequence Analysis of the Boundaries of the T-DNA," *The Plant Journal*, 6(2):271-282, 1994.

Karlin S. et al., "Applications and Statistics for Multiple High-Scoring Segments in Molecular Sequences," *Proc. Natl. Acad. Sci. USA*, vol. 90, pp. 5873-5877, Jun. 1993.

Kikuchi, Y et al., "Site-Specific Cleavage of Natural mRNA Sequences by Newly Designed Hairpin Catalytic RNAs," *Nucleic Acids Research*, 19(24):6751-6755, 1991.

Kikuchi, Y., "Ribozymes: Types and in vivo Activity—Hammerhead and Hairpin Ribozymes," *Kagaku and Seibutsu*, 30(2):112-118, 1992.

Koizumi, M. et al., "Construction of Series of Several Self-Cleaving RNA Duplexes using Synthetic 21-mers," *FEBS Letters*, 227(2):228-230, Feb. 1988.

Koizumi, M. et al., "Cleavage of Specific Sites of RNA Designed Ribozymes," *FEBS Letters*, 239(2):285-288, Nov. 1988.

Koizumi, M. et al., "Design of RNA Enzymes Distinguishing a Single Base Mutation in RNA," *Nucleic Acids Research*, 17(17):7059-7071, 1989.

Koizumi, M. et al., "Ribozyme for Sequence-Dependent Cleavage of Target RNA," *Tanpakushitsu Kakusan Kosho*, vol. 35, pp. 2191-2200, 1990.

Kramer, W. et al., "Oligonucleotide-Directed Construction of Mutations via Gapped Duplex DNA," *Methods in Enzymology*, vol. 154, pp. 350-367, 1987.

Lin, h. et al., "Detection Via Molecular Markers of Epistatic Interactions in Expression Among Rice Photoperiod Sensitivity Genes Hd1, Hd2, and Hd3," in *Proceedings of the Plant & Animal Genome VII Conference*, San Diego, CA, Jan. 17-21, 1991. p. 322.

Mandel, M., "Calcium-Dependent Bacteriophage DNA Infection," *J. Mol. Biol.*, vol. 53. pp. 159-162, 1970.

Martienssen, R., "epigenetic Phenomena: Paramutation and Gene Silencing in Plants," *Current Biology*, 6(7):810-813, 1996.

Okumoto, Y. et al., "No. 120: Location of the Late Heading-Time Gene Locus E3," *Japanese J. of Breeding*, 47(Suppl. 1):31, 1987.

Okumoto, Y. et al., "Analysis of a Rice Variety Taichung 65 and its Isogenic Early-Heading Lines late for Late-Heading Genes E1, E2, E3" *Japan J. Breeding*, vol. 42, pp. 415-429, 1992.

Hirashima, A. et al., "7. Regulation of Gene Expression by Antisense RNA," pp. 319-347, 1993.

Saiki, R. et al., "Enzymatic Amplification of β-Globin Genomic Sequences and Restriction Site Analysis for Diagnosis if Sickle Cell Anemia," *Science*, vol. 230, pp. 1350-1354, 1985.

Saiki, R. et al., "Primer-Directed Enzymatic Amplification of DNA with a Thermostable DNA Polymerase," *Science*, vol. 239, pp. 487-491, 1988.

Smyth, D., "Gene Silencing: Cosuppression at a Distance," *Current Biology*, 7(12):R793-R795, 1997.

Southern, E., "Detection of Specific Sequences Among DNA Fragments Separated by Gel Electrophoresis," *J. Mol. Biol.*, vol. 98, pp. 503-517, 1975.

Taira, K. et al., "Construction of A Novel Artificial -Ribozyme-Releasing Plasmid," *Protein Engineering*, 3(8):733-737, 1990.

Taira, K. et al., "Construction of a Novel RNA-Transcription-Trimming Plasmid which can be used both in vitro in place of run-off and (G)-Free Transcriptions and in vivo as Multi-Sequences Transcription Vectors," Nucleic Acids Research, 19(19):5125-5130, 1991.

Toki, S. et al., Expression of a Maize Ubiquitin Gene Promoter-bar Chimeric Gene in Transgenic Rice Plants, *Plant Physiol.*, vol. 100, pp. 1503-1507, 1992.

Toki, S., "Rapid and Efficient Agrobacterium—Mediated Transformation in Rice," *Plant Molecular Biology*, 15(1):16-21, 1997.

van der Krol, A. et al., "An Anti-Sense Chalcone Synthase Gene in Transgenic Plants Inhibits Flower Pigmentation," *Nature*, vol. 333, pp. 866-869, 1988.

Yamagata, H. et al., "Analysis of Genes Controlling Heading Time in Japanese Rice," *Rice Genetics*, pp. 351-359, 1986.

Yamamoto, T. et al., Fine Mapping and Characterization of Quantitative Trait Loci of Heading Date in Rice, in *Proceedings of the Plant Genome IV Conference*, San Diego, CA, Jan. 1995, p. 124.

Yokoo, M. et al., "Tight Linkage of Blast-Resistance with Late Maturity Observed in Different Indica Varieties of Rice," *Japan J. Breed*, 21(1):35-39, 1971.

Yuyama, N. et al., "Construction of a tRNA-Embedded-Ribozyme Trimming Plasmid," *Biochem. and Biophys. Res. Comm.*, 186(3):1271-1279, Aug. 14, 1992.

* cited by examiner

PLANT PHOTOPERIOD SENSITIVITY GENE HD1 AND USE OF THE SAME

CROSS-REFERENCE TO RELATED APPLICATION

This application is a U.S. National Phase Application of International Application No. PCT/JP00/07693, filed Nov. 1, 2000, which claims priority to Japan Application No. 11/313846, filed Nov. 4, 1999; where these applications are incorporated herein by reference in their entireties.

TECHNICAL FIELD

The present invention relates to genes involved in plant photoperiod sensitivity, and methods for modifying photoperiod sensitivity in plants using the genes. Methods to modify plant photoperiod sensitivity are useful for plant breeding.

BACKGROUND ART

Generally, heading (flowering) of rice is accelerated by short-day and delayed by long-day conditions. Among known cultivars, typically those from Kyushu and the south of Mainland Japan have strong photoperiod sensitivity whereas cultivars from the Tohoku district or Hokkaido show complete loss of such sensitivity or have extremely weak photoperiod sensitivity. Rice plants that lack the photoperiod sensitivity have a characteristic to flower after a certain length of growth period, and the heading date of the plant does not change with changes of photoperiod. Adaptation of rice plants in particular locations and season drastically changes in accordance with the existence of photoperiod sensitivity in the plant. Thus, modification of photoperiod sensitivity in rice is an important aspect of rice breeding.

In conventional breeding programs, the alteration of the heading date of rice is achieved through methods involving: (1) selection of early maturing varieties or late varieties by crossing; and (2) mutagenesis by radiation and chemicals; and soon. However, such breeding programs require long periods of time to be successful, and bear other problems, such as unpredictability of the degree or direction of the variation in the progeny.

"Photoperiod sensitivity gene" is a generic name for genes that enhance the rice photoperiod sensitivity in the field of rice genetics. The existence of several photoperiod sensitivity genes has been observed to be inherent in mutants and cultivars, and photoperiod sensitivity genes are suggested to exist on loci, for example, such as Se1 locus (chromosome 6; Yokoo and Fujimaki (1971) Japan. J. Breed. 21:35-39), E1 locus (chromosome 7; Tsai, K. H. (1976) Jpn. J. Genet. 51: 115-128; Okumoto, Y. et al. (1992) Jpn. J. Breed. 42: 415-429), E2 locus (unknown), E3 locus (chromosome 3?; Okumoto et al. Japanese Society of Breeding, 91st lecture, Japanese Journal of Breeding 47 (Suppl. 1): 31); and so on (Yamagata et al. (1986) In Rice Genetics, International Rice Research Institute, Manilla, pp 351-359).

Isolation of rice photoperiod sensitivity genes enables the introduction of such genes into arbitrary cultivars by transformation methods to modify the photoperiod sensitivity in these cultivar lines, which ultimately permits regulation of the heading date of the rice. Therefore, breeding using such genes is a particularly efficient yet simple and reliable method as compared to conventional methods.

However, the isolation of genes involved in the photoperiod sensitivity of rice has not yet been reported.

DISCLOSURE OF THE INVENTION

This need in the art led to the present invention, and the object of the present invention is to provide novel plant photoperiod sensitivity genes, specifically genes derived from rice. Another object of the present invention is to modify plant photoperiod sensitivity using such genes to modify the flowering time of the plant. Furthermore, another object of the present invention is to provide methods for assessing plant photoperiod sensitivity.

The present inventors focused specifically on rice, for which a simple method to modify the heading date was desired, and vigorously carried out studies to isolate genes related to rice photoperiod sensitivity.

A quantitative trait locus of rice, Hd1, identified using a progeny derived from a cross between Nipponbare and Kasalath, is known to exist on chromosome 6. Additionally, further to analyses on the Hd1 region (allele for Kasalath) with a genetic background of Nipponbare using nearly isogenic lines (Yamamoto et al. (1996) Abstract for Plant Genome IV. p 124), the Hd1 gene locus has been revealed to involve in photoperiod sensitivity (Lin et al. (1999) Abstract for Plant Genome VII, p 160; Yano et al. Breeding science. Supplement, 47 (2), p 224). Furthermore, considering the chromosomal location, it has been suggested that Hd1 may be on the same gene locus as the previously reported photoperiod sensitivity gene locus Se1; however, to date, no direct proof has been brought forward.

In order to isolate the photoperiod sensitivity gene Hd1 (which has not yet been identified despite confirmation of its existence), the present inventors first performed the linkage analysis and alignment of Hd1 gene region with yeast artificial chromosome (YAC) clones.

Specifically, the inventors performed the linkage analysis of a large scale segregating population, which is indispensable for the isolation of the Hd1 gene. The pooled sampling method was used for linkage analysis. Also, by using the alignment of YAC clones produced by the Rice Genome Research Program (RGP), YAC clones around the Hd1 locus were determined. Furthermore, end DNA fragment of the determined YAC clone Y4836 were isolated, and analyzed as an RFLP marker. As a result, the YAC clone Y4836 comprises the Hd1 gene region (FIGS. 1A-1D).

Furthermore, in order to delimit the candidate region of Hd1 gene, the present inventors performed alignment of the Hd1 gene region using P1-derived artificial chromosome (PAC) clones. Specifically, using DNA markers located around the Hd1 gene region found by the above-described analysis, two PAC clones presumed to carry these nucleotide sequences were selected from the genome library of Nipponbare. In addition, the examination of selected PAC clones by PCR revealed that one of the clones, P0038C5, comprises the nucleotide sequences corresponding to S20418 and Y4836R, completely covering the Hd1 locus (FIGS. 1A-1D).

As a result of nucleotide sequence analysis for PAC clone P0038C5, the inventors succeeded in delimiting the region in which the Hd1 candidate gene may exist to about 12 kb. They also performed gene prediction and homology search for this nucleotide sequence of the candidate region. The inventors found a region with an extremely high analogy to the peroxidase S2539, obtained as rice EST, as well as *Arabidopsis* CO (assumed to be a transcriptional regulatory gene having a zinc finger domain) having functions to promote flowering under long-day conditions.

Further analysis performed for the predicted gene having zinc-finger domain as a candidate of Hd1 gene has revealed mutations (by insertion, deletion, and substitution of nucleotides) at eleven sites within the candidate gene region (ORF) of Kasalath (FIG. 2). In addition, analyses were performed for the candidate gene region of se1 mutant lines HS66 and HS110, as well as Ginbozu which is the parent strain thereof. As a result, it has been revealed that nucleotide sequence of Ginbozu comprising the Se1 gene is completely identical with that of Nipponbare, with the exception of an additional 36-bp sequence and one nucleotide substitution. Mutations were observed in mutant strains HS66 and HS110 as compared with the nucleotide sequence of Ginbozu (FIG. 2). From these results, the candidate gene with zinc finger domain has been judged to be a potential candidate for the Hd1 gene.

Furthermore, expression analysis of the candidate gene for Hd1 revealed that the expression level in a near-isogenic line (NIL(Hd1)), in which the Hd1 gene region had been substituted with chromosome fragment of Kasalath, was remarkably reduced as compared with that in Nipponbare. In Ginbozu, a level of transcript similar to that in Nipponbare was detected. On the other hand, in mutant strains HS66 and HS110, transcripts which are different in size from that in Ginbozu were found. Regarding to the relationship between the transcript and days-to-heading in a paddy field, the present inventors discovered that days-to-heading increased in the case where the normal transcript was found (in Nipponbare and Ginbozu), while the days-to-heading decreased in the case where aberrant transcripts were detected (Table 1). From these results, the inventors concluded that the candidate gene region is indeed the Hd1 gene, and that the Se1 locus is the same as the Hd1 locus.

In order to confirm that Hd1 candidate gene has the function to confer upon the rice plant photoperiod sensitivity, a genome region carrying the gene was introduced into a strain which lacked the photoperiod sensitivity, by substituting the photoperiod sensitivity gene region of Nipponbare with Kasalath type gene. As a result, in individuals into which the candidate gene was integrated, the heading was promoted under short-day conditions. Since, in general, the heading is promoted under short-day conditions by high photoperiod sensitivity, the Hd1 candidate gene was found to have the function to enhance photoperiod sensitivity.

In other words, the present inventors succeeded in isolating a gene involved in photoperiod sensitivity of plants. The present inventors also found that the photoperiod sensitivity of plants can be modified using the gene, and that the photoperiod sensitivity of plants can be assessed by the gene, and finally completed the present invention.

More specifically, this invention provides the following:

(1) a DNA encoding a protein derived from plants that increases the photoperiod sensitivity of plants, said DNA is selected from the group consisting of:

(a) a DNA encoding the protein comprising the amino acid sequence of SEQ ID NO: 1 or 3;

(b) a DNA encoding the protein comprising the amino acid sequence of SEQ ID NO: 1 or 3, wherein one or more of the amino acids are substituted, deleted, added and/or inserted; and (c) a DNA hybridizing under stringent conditions with the DNA consisting of the nucleotide sequence of SEQ ID NO: 2 or 4;

(2) the DNA of (1), wherein the DNA is derived from rice;

(3) a DNA encoding an antisense RNA complementary to the transcription product of the DNA of (1) or (2);

(4) a DNA encoding an RNA having the activity of a ribozyme that specifically digests the transcription product of the DNA of (1) or (2);

(5) a DNA encoding an RNA that represses the expression of the DNA of (1) or (2) upon expression in a plant cell due to a corepressing effect;

(6) a DNA of (1) or (2), wherein the DNA is used to increase the photoperiod sensitivity of plants;

(7) a DNA of any one of (3) to (5), wherein the DNA is used to reduce the photoperiod sensitivity of plants;

(8) a vector comprising the DNA of any one of (1) to (5);

(9) a plant cell transformed with the vector of (8);

(10) a plant transformant comprising the plant cell of (9);

(11) the plant transformant of (10), wherein said plant transformant is rice;

(12) a plant transformant which is a progeny or a clone of the plant transformant of (10) or (11);

(13) a breeding material of the plant transformant of any one of (10) to (12);

(14) a method for producing a plant transformant of (10) or (11), which comprises the following steps of (a) introducing the DNA of (1) or (2) into a plant cell, and (b) regenerating a plant from the plant cell;

(15) a method for increasing the photoperiod sensitivity of plants, said method comprising the step of expressing the DNA of (1) or (2) in cells of the plant body;

(16) the method of (15), wherein the heading of a plant dependent on the photoperiod is delayed by increasing the photoperiod sensitivity of the plant;

(17) a method for decreasing the photoperiod sensitivity of plants, said method comprising the step of repressing the expression of the DNA of (1) or (2) in cells of the plant body, wherein said DNA is endogenous to said plant cell;

(18) the method of (17), wherein the DNA of any one of (3) to (5) is expressed within the cells of the plant body;

(19) the method of (17) or (18), wherein the heading of the plant dependent on the photoperiod is accelerated by the decrease in the photoperiod sensitivity of the plant;

(20) a method of any one of (15) to (19), wherein the plant is rice;

(21) a method for assessing the photoperiod sensitivity of plants, comprising the steps of detecting the presence or absence of the DNA of (1) in the plant;

(22) the method of (21), wherein the plant is rice;

(23) a host cell wherein a vector comprising the DNA of (1) or (2) is inserted;

(24) a protein encoded by the DNA of (1) or (2);

(25) a method for producing the protein of (24) comprising the following steps of: culturing a host cell of (23), allowing the host cell to express a recombinant protein encoded by said DNA, and recovering the recombinant protein from the host cell or the culture supernatant thereof;

(26) an antibody that binds to the protein of (24); and

(27) a DNA comprising at least 15 nucleotides that are complementary to a DNA consisting of the nucleotide sequence of SEQ ID NO: 2 or 4 to a complementary strand thereof.

The present invention provides a DNA encoding a rice plant-derived Hd1 protein. Nucleotide sequence of the Hd1 genomic DNA of Nipponbare is set forth in SEQ ID NO: 2, and amino acid sequence of a protein encoded by the DNA in SEQ ID NO: 1. Furthermore, nucleotide sequence of the Hd1 genomic DNA of Ginbozu is set forth in SEQ ID NO: 4, and amino acid sequence of a protein encoded by the DNA in SEQ ID NO: 3.

Hd1 is one of the quantitative trait loci (QTL) detected by using backcross progeny between Nipponbare and Kasalath, and has been found to exist on chromosome 6. In addition, from experiments using a near-isogenic line of the Hd1 region having the genetic background of Nipponbare, Hd1 locus was known to be a photoperiod sensitivity gene locus. The Hd1 gene acts to decrease the duration required from sowing to heading (days-to-heading) under short-day conditions, and to increase the days-to-heading under long-day conditions. That is, the Hd1 gene of Nipponbare enhances the photoperiod sensitivity of rice plant to modify the plant so as to ripe late in a natural field cultivation (under near long-day conditions). The Hd1 gene has been known to be a gene involved in photoperiod sensitivity of plants and to exist somewhere within the vast region of chromosome 6. However, the Hd6 gene had not been identified nor isolated. After performing complicated examination steps, the present inventors finally identified the region where the gene exists, and succeeded for the first time in isolating the gene as a single gene.

Today, it is an important object to control the heading date of rice in the breeding of rice in Japan. It is important to evade cold weather damage in cold districts due to the early coming of low-temperature of fall. On the other hand, to abridge the labor due to centralization of harvest time in the extensive rice-growing region in the west-south warm area, there is a need to accelerate or to delay the heading date.

The heading date of plants (flowering time) can be delayed by transforming plants with a DNA encoding the Hd1 protein which enhances the photoperiod sensitivity of plants. Alternatively, control of the expression of the DNA using the antisense method or the ribozyme method enables reduced photoperiod sensitivity, and accelerated flowering time of plants. Specifically, the flowering time of plants can be diversified by recombinantly introducing a DNA encoding the Hd1 protein to plants lacking the DNA and by controlling expression of the DNA in cultivars having the DNA using antisense, ribozymes, and such. Thus, new kinds of cultivars can be bred.

DNA encoding the Hd1 protein of the present invention include genomic DNA, cDNA, and chemically synthesized DNA. A genomic DNA and cDNA can be prepared according to conventional methods known to those skilled in the art. More specifically, a genomic DNA can be prepared, for example, as follows: (1) extract genomic DNA from rice cultivars having the photoperiod sensitivity gene (e.g. Nipponbare or Ginbozu); (2) construct a genomic library (utilizing a vector, such as plasmid, phage, cosmid, BAC, PAC, and so on); (3) spread the library; and (4) conduct colony hybridization or plaque hybridization using a probe prepared based on the DNA encoding a protein of the present invention (e.g. SEQ ID NO: 2 or 4). Alternatively, a genomic DNA can be prepared by PCR, using primers specific to a DNA encoding the protein of s present invention (e.g. SEQ ID NO: 2 or 4). On the other hand, cDNA can be prepared, for example, as follows: (1) synthesize cDNAs based on mRNAs extracted from rice cultivars having the photoperiod sensitivity gene (e.g. Nipponbare or Ginbozu); (2) prepare a cDNA library by inserting the synthesized cDNA into vectors, such as λZAP; (3) spread the cDNA library; and (4) conduct colony hybridization or plaque hybridization as described above. Alternatively, cDNA can be also prepared by PCR.

The present invention includes DNAs encoding proteins (Nipponbare or Ginbozu) functionally equivalent to the Hd1 protein of SEQ ID NO: 1 or 3. Herein, the term "functionally equivalent to the Hd1 protein" indicates that the object protein has the function of enhancing the photoperiod sensitivity of plants. Such DNA is derived preferably from monocotyledonous plants, more preferably from Gramineae, and most preferably from rice.

Examples of such DNAs include those encoding mutants, derivatives, alleles, variants, and homologues comprising the amino acid sequence of SEQ ID NO: 1 or 3 wherein one or more amino acids are substituted, deleted, added and/or inserted.

Examples of methods for preparing a DNA encoding a protein comprising altered amino acids well known to those skilled in the art include the site-directed mutagenesis (Kramer, W. and Fritz, H.-J., (1987) "Oligonucleotide-directed construction of mutagenesis via gapped duplex DNA." Methods in Enzymology, 154: 350-367). The amino acid sequence of a protein may also be mutated in nature due to the mutation of a nucleotide sequence. A DNA encoding proteins having the amino acid sequence of a natural Hd1 protein wherein one or more amino acids are substituted, deleted, and/or added are also included in the DNA of the present invention, so long as they encode a protein functionally equivalent to the natural Hd1 protein (SEQ ID NO: 1 or 3). Additionally, nucleotide sequence mutants that do not give rise to amino acid sequence changes in the protein (degeneracy mutants) are also included in the DNA of the present invention.

Assessment of whether a DNA encodes a protein that enhances the photoperiod sensitivity of plants or not can be performed as follows: The most general method involves transforming with the DNA a plant grown in a growth cabinet wherein the length of day can be changed. More specifically, plants are grown under short-day condition (generally, 9 to 10 hours) or long-day condition (14 to 16 hours), and the number of days required from seeding to flowering (when the plant is rice, from seeding to heading) is compared between plants grown under these different conditions. Plants that show no difference in the number of days-to-heading between the long-day and short-day conditions are determined to lack photoperiod sensitivity. Plants that show a difference in the number of days-to-heading between the two conditions are determined to have photoperiod sensitivity, and the difference is considered as the degree of photoperiod sensitivity of the plant. In those cases where a growth cabinet is not available, the assessment can be also performed by growing plants in fields and in greenhouses with natural day length. Specifically, plants are seeded every 20th day and are grown under natural day length under constant temperature to determine days needed for flowering in respective plants. Generally, the heading of rice cultivars with strong photoperiod sensitivity are accelerated when seeded during August to February, and those seeded between April to July are delayed. On the other hand, days-to-heading in rice cultivars having weak photoperiod sensitivity is not influenced by the season of seeding and doesn't change greatly according to day length.

A DNA encoding a protein functionally equivalent to the Hd1 protein described in SEQ ID NO: 1 or 3 can be produced, for example, by methods well known to those skilled in the art including: methods using hybridization techniques (Southern, E. M.: Journal of Molecular Biology, Vol. 98, 503, 1975.); and polymerase chain reaction (PCR) techniques (Saiki, R. K. et al. Science, vol. 230, 1350-1354, 1985; Saiki, R. K. et al. Science, vol. 239, 487-491, 1988).

That is, it is routine for a person skilled in the art to isolate a DNA with high homology to the Hd1 gene from rice and other plants using the nucleotide sequence of the Hd1 gene (SEQ ID NO: 2 or 4) or parts thereof as a probe, and oligonucleotides hybridizing specifically to the nucleotide sequence of Hd1 gene (SEQ ID NO: 2 or 4) as a primer. Such DNA encoding proteins functionally equivalent to the Hd1 protein, obtainable by hybridization techniques or PCR techniques, are included in the DNA of this invention.

Hybridization reactions to isolate such DNAs are preferably conducted under stringent conditions. Stringent hybridization conditions of the present invention include conditions such as: 6 M urea, 0.4% SDS, and 0.5×SSC; and those which yield a similar stringency to the conditions. DNAs with higher homology are expected when hybridization is performed under conditions with higher stringency, for example, 6 M urea, 0.4% SDS, and 0.1×SSC. Those DNAs isolated under such conditions are expected to encode a protein having a high amino acid level homology with Hd1 protein (SEQ ID NO: 1 or 3). Herein, high homology means an identity of at least 50% or more, more preferably 70% or more, and much more preferably 90% or more (e.g. 95% or more), through the entire amino acid sequence. The degree of homology of one amino acid sequence or nucleotide sequence to another can be determined by following the algorithm BLAST by Karlin and Altschl (Proc. Natl. Acad. Sci. USA, 90: 5873-5877, 1993). Programs such as BLASTN and BLASTX were developed based on this algorithm (Altschul et al. J. Mol. Biol. 215: 403-410, 1990). To analyze a nucleotide sequences according to BLASTN based on BLAST, the parameters are set, for example, as score=100 and word length=12. On the other hand, parameters used for the analysis of amino acid sequences by the BLASTX based on BLAST include, for example, score=50 and word length=3. Default parameters of each program are used when using BLAST and Gapped BLAST program. Specific techniques for such analysis are known in the art. See, for example, the web page for the National Center for Biotechnology Information.

The DNA of the present invention can be used, for example, to prepare recombinant proteins, produce plant transformants with altered photoperiod sensitivity, and so on.

A recombinant protein is usually prepared by inserting a DNA encoding a protein of the present invention into an appropriate expression vector, introducing the vector into an appropriate cell, culturing the transformed cells, allowing the cells to express the recombinant protein, and purifying the expressed protein. A recombinant protein can be expressed as a fusion protein with other proteins so as to be easily purified, for example, as a fusion protein with maltose binding protein in *Escherichia coli* (New England Biolabs, USA, vector pMAL series), as a fusion protein with glutathione-S-transferase (GST) (Amersham Pharmacia Biotech, vector pGEX series), or tagged with histidine (Novagen, pET series). The host cell is not limited so long as the cell is suitable for expressing the recombinant protein. It is possible to utilize yeasts or various animal, plant, or insect cells besides the above described *E. coli*. A vector can be introduced into a host cell by a variety of methods known to one skilled in the art. For example, a transformation method using calcium ions (Mandel, M. and Higa, A. (1970) Journal of Molecular Biology, 53, 158-162, Hanahan, D. (1983) Journal of Molecular Biology, 166, 557-580) can be used to introduce a vector into *E. coli*. A recombinant protein expressed in host cells can be purified and recovered from the host cells or the culture supernatant thereof by known methods. When a recombinant protein is expressed as a fusion protein with maltose binding protein or other partners, the recombinant protein can be easily purified by affinity chromatography.

The resulting protein can be used to prepare an antibody that binds to the protein. For example, a polyclonal antibody can be prepared by immunizing immune animals, such as rabbits, with a purified protein of the present invention or its portion, collecting blood after a certain period, and removing clots. A monoclonal antibody can be prepared by fusing myeloma cells with the antibody-forming cells of animals immunized with the above protein or its portion, isolating a monoclonal cell expressing a desired antibody (hybridoma), and recovering the antibody from the cell. The obtained antibody can be utilized to purify or detect a protein of the present invention. Accordingly, the present invention includes antibodies that bind to proteins of the invention.

A plant transformant with increased photoperiod sensitivity can be created using DNAs of the present invention. More specifically, a DNA encoding a protein of the present invention is inserted into an appropriate vector; the vector is introduced into a plant cell; and then, the resulting transformed plant cell is regenerated. The photoperiod sensitivity gene Hd1, isolated by the present inventors, functions to enhance the photoperiod sensitivity of rice, and can delay the heading date of rice. Therefore, the heading date of arbitrary cultivars can be controlled by transforming the cultivars with the gene and expressing the same. The time needed for transformation is remarkably short as compared to ordinary gene transfer by crossing. Furthermore, the fact that the transformation doesn't accompany other characteristic changes is also beneficial. Genes controlling the heading date of rice are newly identified and isolated herein, and controlling of heading date of rice is enabled for the first time by the present invention.

On the other hand, a plant transformant with reduced photoperiod sensitivity can be created using DNA that represses the expression of a DNA encoding a protein of the present invention: wherein the DNA is inserted into an appropriate vector, the vector is introduced into a plant cell, and then, the resulting transformed plant cell is regenerated. The phrase "repression of expression of DNA encoding a protein of the present invention" includes repression of gene transcription as well as repression of translation into protein. It also includes not only the complete inability of expression of DNA but also reduction of expression.

The expression of a specific endogenous gene in plants can be repressed by methods utilizing antisense technology, which are commonly used in the art. Ecker et al. were the first to demonstrate the antisense effect of an antisense RNA introduced by electroporation in plant cells by using the transient gene expression method (J. R. Ecker and R. W. Davis (1986) Proc. Natl. Acad. Sci. USA 83: 5372). Thereafter, the target gene expression was reportedly reduced in tobacco and petunias by expressing antisense RNAs (A. R. van der Krol et al. (1988) Nature 333: 866). The antisense technique has now been established as a means to repress target gene expression in plants.

Multiple factors cause antisense nucleic acid to repress the target gene expression. These include: inhibition of transcription initiation by triple strand formation; repression of transcription by hybrid formation at the site where the RNA polymerase has formed a local open loop structure; transcription inhibition by hybrid formation with the RNA being synthesized; repression of splicing by hybrid formation at the junction between an intron and an exon; repression of splicing by hybrid formation at the site of spliceosome formation; repression of mRNA translocation from the nucleus to the cytoplasm by hybrid formation with mRNA; repression of splicing by hybrid formation at the capping site or at the poly A addition site; repression of translation initiation by hybrid formation at the binding site for the translation initiation factors; repression of translation by hybrid formation at the site for ribosome binding near the initiation codon; inhibition of peptide chain elongation by hybrid formation in the translated region or at the polysome binding sites of mRNA; and repression of gene expression by hybrid formation at the sites of interaction between nucleic acids and proteins. These factors repress the target gene expression by inhibiting the process of transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)," Nihon Seikagakukai Hen (The Japanese Biochemical Society), Tokyo Kagaku Dozin, pp. 319-347, (1993)).

An antisense sequence of the present invention can repress the target gene expression by any of the above mechanisms. In one embodiment, if an antisense sequence is designed to be complementary to the untranslated region near the 5' end of the gene's mRNA, it will effectively inhibit translation of a gene. It is also possible to use sequences complementary to the coding regions or to the untranslated region on the 3' side. Thus, the antisense DNA used in the present invention include DNA having antisense sequences against both the untranslated regions and the translated regions of the gene. The antisense DNA to be used is connected downstream from an appropriate promoter, and, preferably, a sequence containing the transcription termination signal is connected on the 3' side. The DNA thus prepared can be transfected into the desired plant by known methods. The sequence of the antisense DNA is preferably a sequence complementary to the endogenous gene of the plant to be transformed or a part thereof, but it need not be perfectly complementary so long as it can effectively inhibit the gene expression. The transcribed RNA is preferably at least 90%, and most preferably at least 95% complementary to the transcribed products of the target gene. In order to effectively inhibit the expression of the target gene by means of an antisense sequence, the antisense DNA should be at least 15 nucleotides long, more preferably at least 100 nucleotides long, and still more preferably at least 500 nucleotides long. The antisense DNA to be used is generally shorter than 5 kb, and preferably shorter than 2.5 kb.

DNA encoding ribozymes can also be used to repress the expression of endogenous genes. A ribozyme is an RNA molecule that has catalytic activities. There are many ribozymes having various activities. Research on the ribozymes as RNA cleaving enzymes has enabled the design of a ribozyme that site-specifically cleaves RNA. While some ribozymes of the group I intron type or the M1RNA contained in RNaseP consist of 400 nucleotides or more, others belonging to the hammerhead type or the hairpin type have an activity domain of about 40 nucleotides (Makoto Koizumi and Eiko Ohtsuka (1990) Tanpakushitsu Kakusan Kohso (Nucleic acid, Protein, and Enzyme) 35: 2191).

The self-cleavage domain of a hammerhead type ribozyme cleaves at the 3' side of C15 of the sequence G13U14C15. Formation of a nucleotide pair between U14 and A at the ninth position is considered important for the ribozyme activity. Furthermore, it has been shown that the cleavage also occurs when the nucleotide at the 15th position is A or U instead of C (M. Koizumi et al (1988). FEBS Lett. 228: 225). If the substrate binding site of the ribozyme is designed to be complementary to the RNA sequences adjacent to the target site, one can create a restriction-enzyme-like RNA cleaving ribozyme which recognizes the sequence UC, UU, or UA within the target RNA (M. Koizumi et al. (1988) FEBS Lett. 239: 285; Makoto Koizumi and Eiko Ohtsuka (1990) Tanpakushitsu Kakusan Kohso (Protein, Nucleic acid, and Enzyme), 35: 2191; M. Koizumi et al. (1989) Nucleic Acids Res. 17: 7059). For example, in the coding region of the Hd1 gene (SEQ ID NO: 2 or 4), there are a plurality of sites that can be used as the ribozyme target.

The hairpin type ribozyme is also useful in the present invention. A hairpin type ribozyme can be found, for example, in the minus strand of the satellite RNA of tobacco ringspot virus (J. M. Buzayan, Nature 323: 349 (1986)). This ribozyme has also been shown to target-specifically cleave RNA (Y. Kikuchi and N. Sasaki (1992) Nucleic Acids Res. 19: 6751; Yo Kikuchi (1992) Kagaku To Seibutsu (Chemistry and Biology) 30: 112).

The ribozyme designed to cleave the target is fused with a promoter, such as the cauliflower mosaic virus 35S promoter, and with a transcription termination sequence, so that it will be transcribed in plant cells. However, if extra sequences have been added to the 5' end or the 3' end of the transcribed RNA, the ribozyme activity can be lost. In this case, one can place an additional trimming ribozyme, which functions in cis to perform the trimming on the 5' or the 3' side of the ribozyme portion, in order to precisely cut the ribozyme portion from the transcribed RNA containing the ribozyme (K. Taira et al. (1990) Protein Eng. 3: 733; A. M. Dzaianott and J. J. Bujarski (1989) Proc. Natl. Acad. Sci. USA 86: 4823; C. A. Grosshands and R. T. Cech (1991) Nucleic Acids Res. 19: 3875; K. Taira et al. (1991) Nucleic Acid Res. 19: 5125). Multiple sites within the target gene can be cleaved by arranging these structural units in tandem to achieve greater effects (N. Yuyama et al., Biochem. Biophys. Res. Commun. 186: 1271 (1992)). By using such ribozymes, it is possible to specifically cleave the transcription products of the target gene in the present invention, thereby repressing the expression of the gene.

Endogenous gene expression can also be repressed by co-repression through the transformation by DNA having a sequence identical or similar to the target gene sequence. Co-repression refers to the phenomenon in which, when a gene having a sequence identical or similar to the target endogenous gene sequence is introduced into plants by transformation, expression of both the introduced exogenous gene and the target endogenous gene becomes repressed. Although the detailed mechanism of co-repression is unknown, it is frequently observed in plants (Curr. Biol. 7: R793, 1997, Curr. Biol. 6: 810, 1996). For example, if one wishes to obtain a plant body in which the Hd1 gene is co-repressed, the plant in question can be transformed with a vector DNA designed so as to express the Hd1 gene or DNA having a similar sequence to select a plant having the Hd1 mutant character, i.e., a plant with reduced photoperiod sensitivity, among the resultant plants. The gene to be used for co-repression does not need to be completely identical to the target gene, but it should have at least 70% or more sequence identity, preferably 80% or more sequence identity, and more preferably 90% or more (e.g. 95% or more) sequence identity. Sequence identity may be determined by above-described method.

In addition, endogenous gene expression in the present invention can also be repressed by transforming the plant with a gene having the dominant negative phenotype of the target gene. A gene having the dominant negative phenotype means a gene which, when expressed, can eliminate or reduce the activity of the wild type endogenous gene inherent to the plant.

Vectors used for the transformation of plant cells are not limited so long as the vector can express inserted genes in plant cells. For example, vectors comprising promoters for constitutive gene expression in plant cells (e.g., cauliflower mosaic virus 35S promoter); and promoters inducible by exogenous stimuli can be used. The term "plant cell" used herein includes various forms of plant cells, such as cultured cell suspensions, protoplasts, leaf sections, and callus.

A vector can be introduced into plant cells by known methods, such as the polyethylene glycol method, electroporation, *Agrobacterium* mediated transfer, and particle bombardment. Plants can be regenerated from transformed plant cells by known methods depending on the type of the plant cell (Toki et al., (1995) Plant Physiol. 100:1503-1507). For example, transformation and regeneration methods for rice plants include: (1) introducing genes into protoplasts using polyethylene glycol, and regenerating the plant body (suitable for indica rice cultivars) (Datta, S. K. (1995) in "Gene Transfer To Plants", Potrykus I and Spangenberg Eds. pp 66-74); (2) introducing genes into protoplasts using electric pulse, and regenerating the plant body (suitable for japonica rice cultivars) (Toki et al (1992) Plant Physiol. 100, 1503-1507); (3) introducing genes directly into cells by the particle bombardment, and regenerating the plant body (Christou et al. (1991) Bio/Technology, 9: 957-962); (4) introducing genes using *Agrobacterium*, and regenerating the plant body (Hiei et al. (1994) Plant J. 6: 271-282); and so on. These methods are already established in the art and are widely used in the technical field of the present invention. Such methods can be suitably used for the present invention.

Once a transformed plant, wherein the DNA of the present invention is introduced into the genome, is obtained, it is possible to gain descendants from that plant body by sexual or vegetative propagation. Alternatively, plants can be mass-produced from breeding materials (for example, seeds, fruits, ears, tubers, tubercles, tubs, callus, protoplast, etc.) obtained from the plant, as well as descendants or clones thereof. Plant cells transformed with the DNA of the present invention, plant bodies including these cells, descendants and clones of the plant, as well as breeding materials obtained from the plant, its descendant and clones, are all included in the present invention.

The flowering time in plants with modified photoperiod sensitivity, prepared as above, is different from that of wild-type plants. For example, plants into which a DNA encoding the Hd1 protein is introduced have increased photoperiod sensitivity, and flowering time of the plant is delayed under paddy field conditions. On the other hand, plants wherein the expression of the DNA encoding the Hd1 protein is repressed due to the introduction of antisense DNAs, have reduced photoperiod sensitivity and the day-to-heading of the plant is decreased. Thus, the time needed for flowering of plants can be regulated by controlling the expression of the Hd1 gene. According to the present invention, the heading date of rice, a valuable crop, can be closely controlled, which is extremely beneficial in the breeding of rice cultivars adapted to a particular environment.

Furthermore, the present invention also provides a method for assessing photoperiod sensitivity of plants. The present inventors investigated the relationship between the transcript of the Hd1 gene and days-to-heading in a paddy field, and then found that days-to-heading increased when the normal transcript thereof was detected (in Nipponbare and Ginbozu), and that it decreased when aberrant transcripts were found (Example 5). These results indicate that whether the functional Hd1 protein is expressed or not is a factor that determines the photoperiod sensitivity level in plants. A method for assessing photoperiod sensitivity of plant in the present invention is based on this finding, and is characterized by the step of detecting whether a test plant carries a DNA encoding a functional Hd1 protein.

Whether a plant carries a DNA encoding the functional Hd1 protein or not may be assessed, for example, by detecting, as a polymorphism, the structural difference in the region corresponding to Hd1 in the genomic DNA.

The assessment of the photoperiod sensitivity of plants using the method of the present invention is effective, for example, in breeding plants by crossing. That is, when the introduction of photoperiod sensitivity character is undesirable, crossing with plants having photoperiod sensitivity can be avoided by the present invention. On the contrary, when the introduction of a photoperiod sensitivity character is desired, crossing with cultivars having photoperiod sensitivity is enabled by the present invention. Furthermore, the present method is also useful in selecting plants from crossed progeny plants. Determination of the photoperiod sensitivity of plants at the gene sequence is simple and reliable as compared to a determination based on the phenotype of the plant. Thus, the method for assessment of the photoperiod sensitivity of the present invention contributes markedly to progress in breeding methods for plants.

Further, the present invention provides DNAs comprising at least 15 nucleotides that are complementary to a DNA of the present invention consisting of the nucleotide sequence of SEQ ID NO: 2 or 4, or to the complementary strand thereof. Herein, the term "complementary strand" is defined as one strand of a double stranded DNA composed of A:T and G:C base pairs to the other strand. In addition, "complementary" is defined as not only those completely matching within a region of at least 15 continuous nucleotides, but also having a homology of at least 70%, preferably at least 80%, more preferably 90%, and even more preferably 95% or higher within that region. Such DNAs are useful as probes to detect or isolate a DNA of the present invention, or as primers to amplify a DNA of the present invention.

A shows a linkage map produced with a segregating population of 1,505 individuals.

B shows an alignment of yeast artificial chromosome (YAC) clones.

C shows an alignment of P1-derived artificial chromosome (PAC) clones.

D shows the candidate region of Hd1 gene and predicted Hd1 genes as well as results of homology search thereof.

Figures 1A, 1B, 1C, 1D:
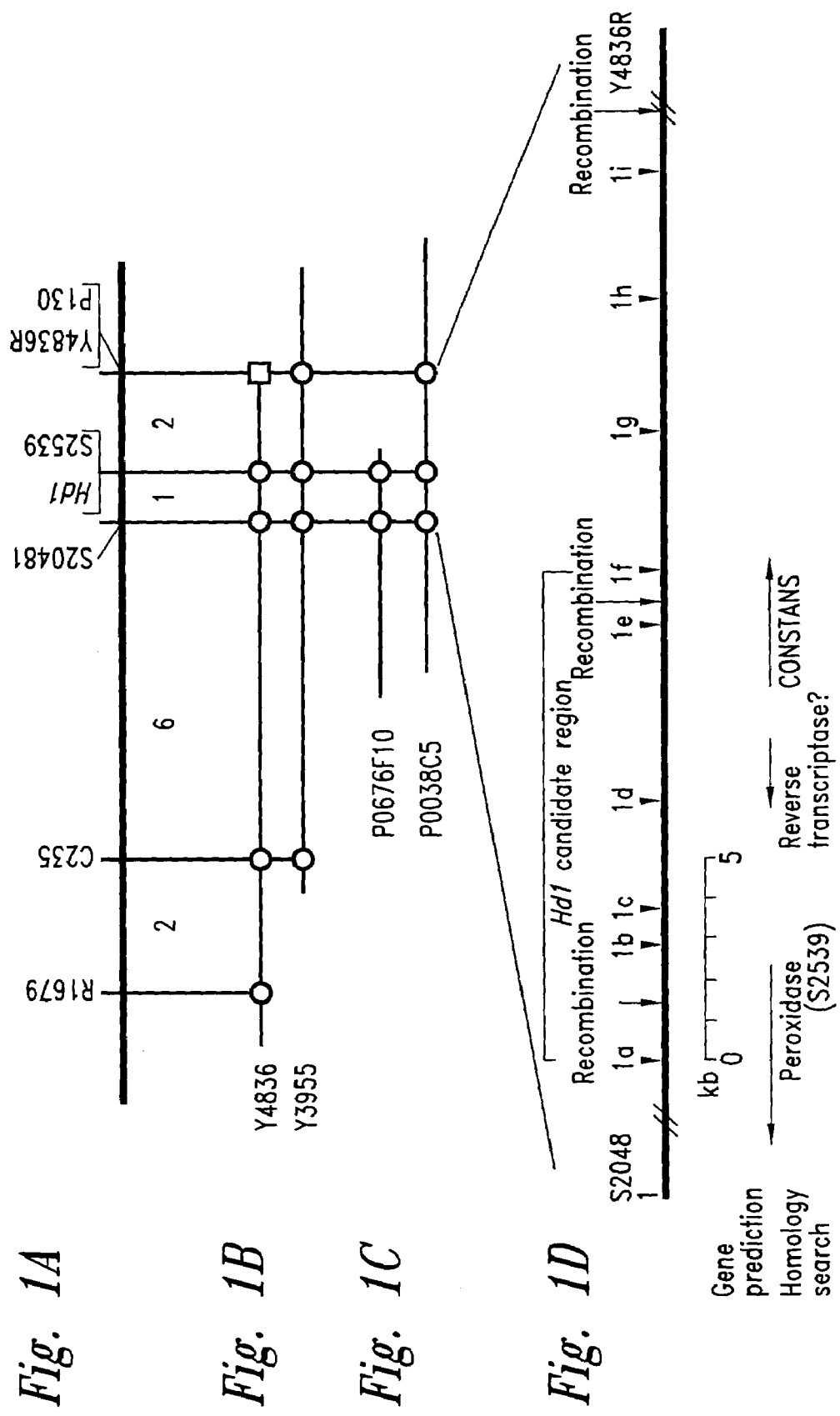
FIGS. 1A-1D show fine-scale linkage maps of the Hd1 gene region, and alignments of YAC as well as those of genomic clones.
Figure 2:
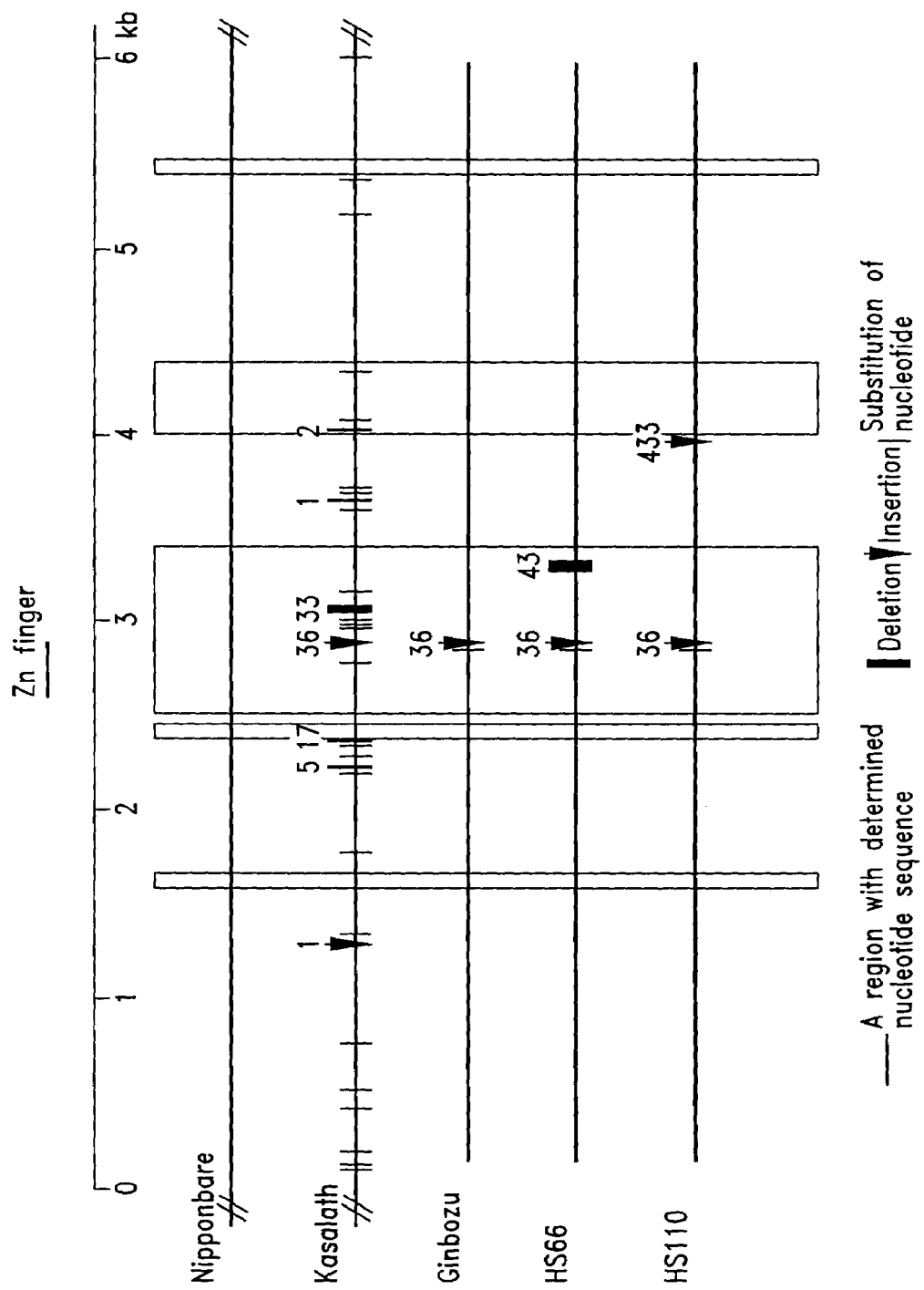

FIG. 2 depicts a comparison of nucleotide sequences of the Hd1 candidate gene regions. Nipponbare and Ginbozu have functional Hd1 genes, while Kasalath has an Hd1 gene with its function being reduced or deleted. HS66 and HS110 are mutant lines with the photoperiod sensitivity of Se1 locus being lost induced by γ ray irradiation. Regions surrounded by rectangular lines indicate the regions assumed to be exons as a result of gene prediction. Numerals above the detected mutation sites represent the number of nucleotides inserted or deleted.

Figure 3:
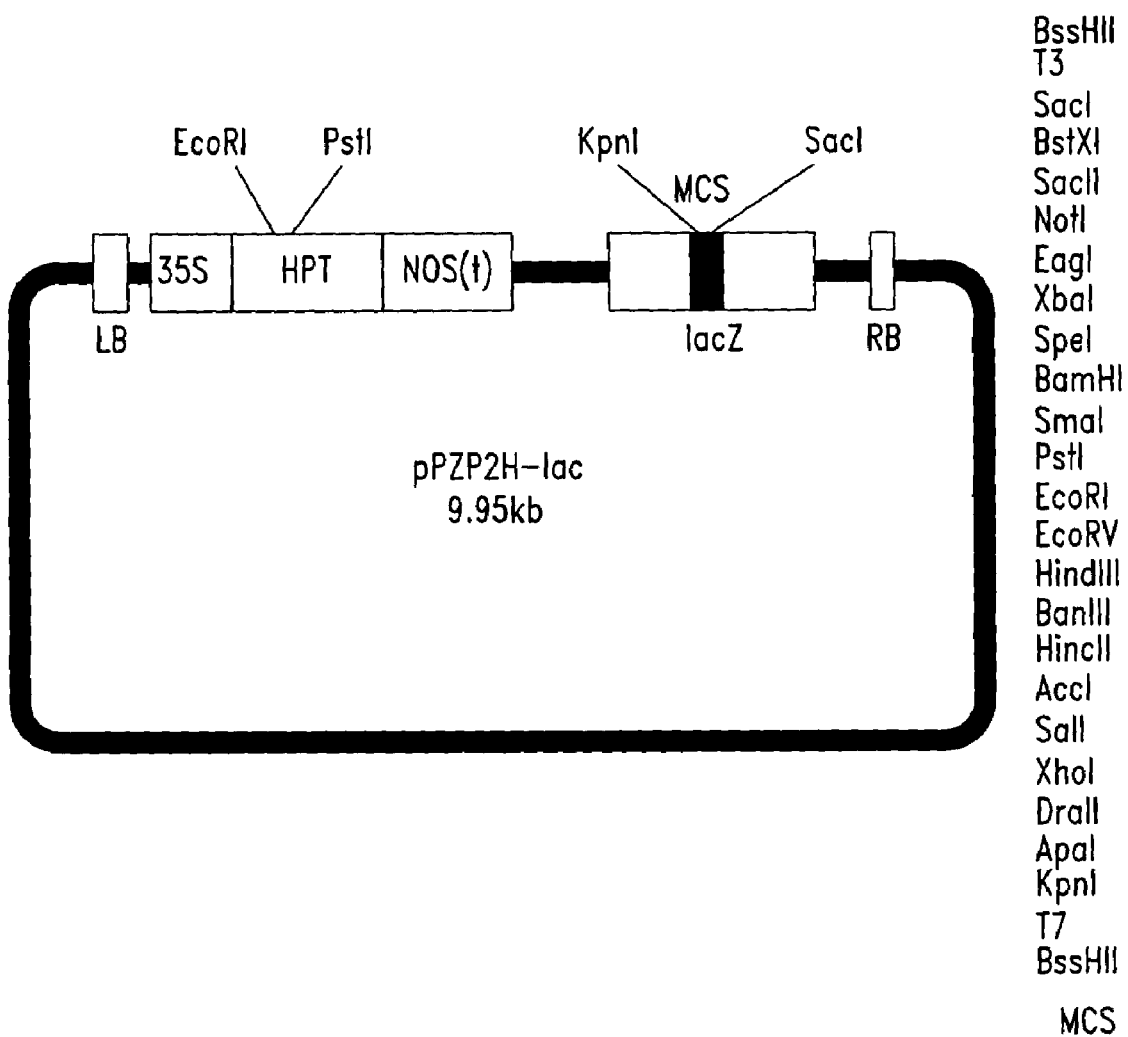

FIG. 3 represents a vector used for complementation assay by transformation.

Figure 4:
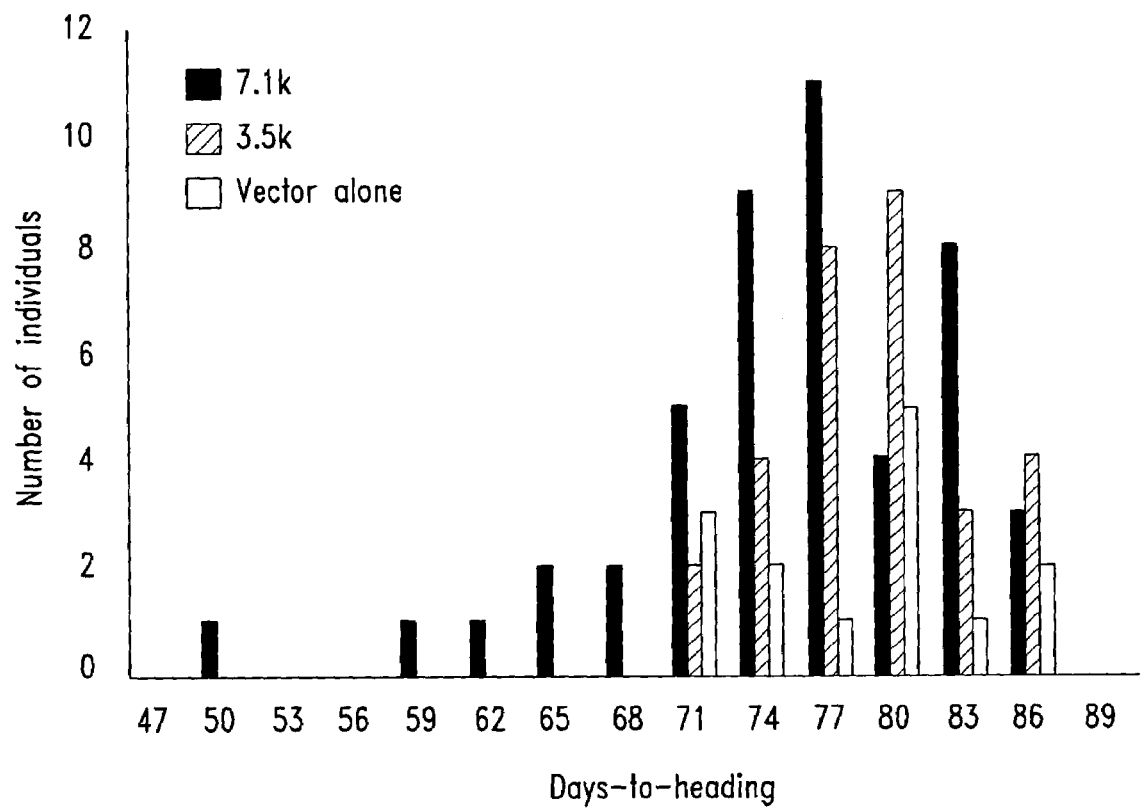

FIG. 4 shows changes in the duration required for the heading in a population of transformed individuals into which a 7.1-kb genomic DNA fragment containing the Hd1 candidate gene region had been introduced.

Figure 5:
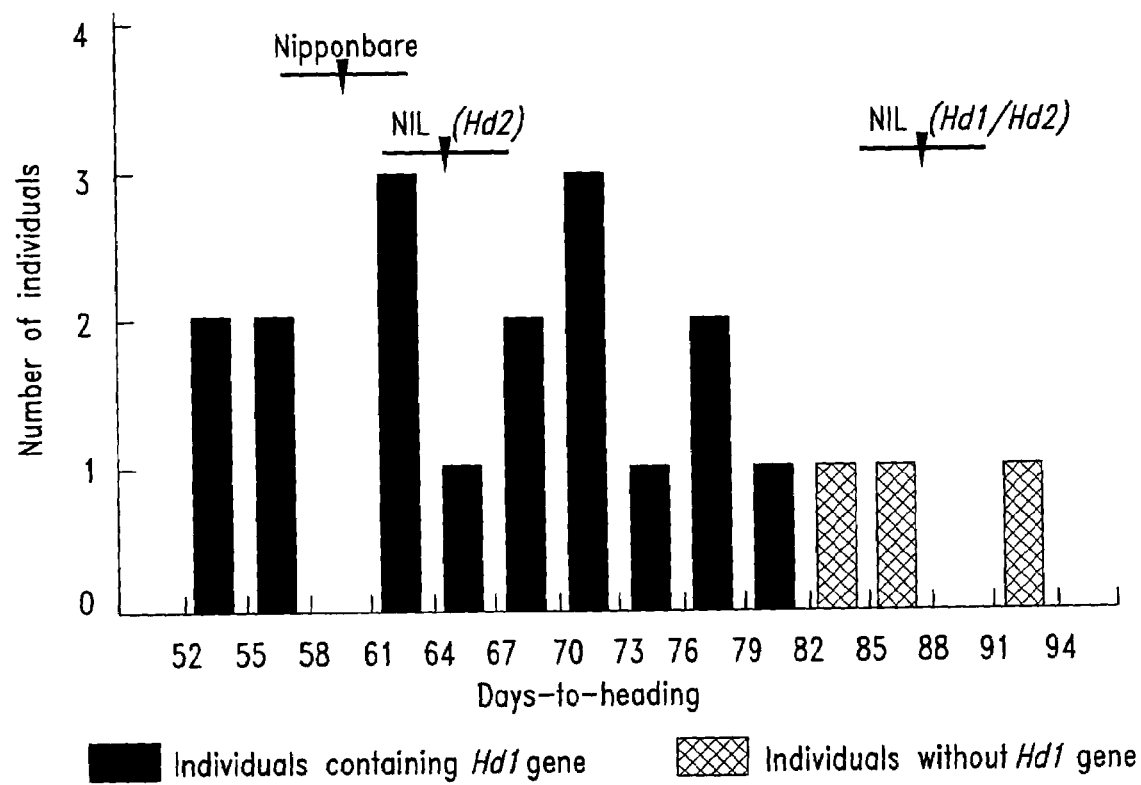

FIG. 5 shows the duration required for the heading in a population of self-fertilized progeny (T1) of transformed individuals into which a 7.1-kb genomic DNA fragment containing the Hd1 candidate gene region had been introduced.

BEST MODE FOR CARRYING OUT THE INVENTION

The present invention is specifically illustrated below with reference to Examples, but it is not construed as being limited thereto.

EXAMPLE 1

Alignment of Hd1 Gene Region with Fine-Scale Linkage Analysis and Yeast Artificial Chromosome (YAC) Clones A fine-scale linkage analysis of the Hd1 region indispensable for the map-based cloning was performed using a large segregating population. As a population for the linkage analysis, backcrossed progeny $BC_3F_3$ generation derived from a cross between Nipponbare and Kasalath, in which Hd1 region are segregated, was used. For linkage analysis, the pooled sampling method was used. That is, about 8,000 of Hd1-region segregating $BC_3F_3$ individuals were cultivated in a paddy field, and investigated for heading date thereof to select, from segregants, 1,505 of the early-ripening individuals which were assumed to be homozygous for Kasalath allele at the Hd1 locus. DNA was extracted from pools of leaves derived from 5 individuals selected above, and individuals having chromosomes with recombinations occurred in the Hd1 region were chosen. RFLP markers used in the recombinant individual selection were R1679 and P130. As a result, nine and two recombinant individuals were selected between R1679 and Hd1 as well as between Hd1 and P130, respectively (FIGS. 1A-1D).

A further fine-scale linkage analysis using DNA markers thought to exist around Hd1 revealed that the Hd1 locus was located between RFLP markers S20481 and P130, but no recombinant was found between S2539 and Hd1 (FIGS. 1A-1D). One and two recombinant individuals useful for delimiting the genomic candidate region of the Hd1 gene were found between S20481 and Hd1, and between Hd1 and P130, respectively.

Based on the information on alignment map of YAC clones prepared in the study of rice genome, YAC clones comprising nucleotide sequences of DNA markers C235, S20481, and S2539 adjacent to the Hd1 locus were identified. Furthermore, when the end DNA fragment of the identified YAC clone, Y4836, was isolated by the cassette method, and analyzed as an RFLP marker, the end DNA clone Y4836R was co-segregated with the RELP marker P130, revealing that the YAC clone Y4836R comprises the Hd1 locus (FIGS. 1A-1D).

EXAMPLE 2

Alignment of Hd1 Gene Region Using P1-Derived Artificial Chromosome (PAC) Clones Using a set of STS (sequence-tagged-site) primers derived from the RFLP markers S20481 (0.74-kb amplified genomic fragment) and S2539 (1.9-kb amplified genomic fragment) around the Hd1 locus, a PAC clone library of Nipponbare genome (insert length: 112 kb on average, 18432 clones; corresponding to about 4.5 times in size of the rice genome) prepared in the Rice Genome Research Program (RGP) was screened. STS primers were produced with "5'-GGA CTG GGT GAA GAA GAT-3' (SEQ ID NO: 5)" and "5'-CCT TGT CCT CTC CTC TTG-31 (SEQ ID NO: 6)" for S20481, and "5'-GTA GAG TGA TGA CAA AAT GAC AA-3' (SEQ ID NO: 7)" and "5'-GGA CTG AGA TGG AAT GTG CT-3' (SEQ ID NO: 8)" for S2539. As a result, two clones, P0676F10 and P0038C5, were selected. Furthermore, whether these PAC clones have the nucleotide sequences corresponding to RFLP markers Y4836R and P130 was investigated by PCR. As a result, it was revealed that the PAC clone P0038C5 has the nucleotide sequence corresponding to Y4836R, completely covering the Hd1 locus (FIGS. 1A-1D).

EXAMPLE 3

Determination of the Candidate Gene by Nucleotide Sequence Analysis

Nucleotide sequence of the PAC clone P0038C5 which is presumed to carry the Hd1 gene was analyzed. For the nucleotide sequence analysis, the insert DNA of P0038C5 (including vector) was ultrasonicated to prepare a sublibrary of inserts comprising 2.5 kb and 5 kb fragments on average. Nucleotide sequences of 2,000 clones arbitrarily selected from this sublibrary were analyzed, and assembled by using the computer software Phred/Phrap. Using information on the nucleotide sequences within the candidate genomic region specified by linkage analysis, further CAPS (Cleaved Amplified Polymorphic Sequence) markers were newly produced to delimit the candidate region. The Hd1 gene was co-segregated with following CAPS markers used as primers: 1b (restriction enzyme SspI) "5'-AAG CAA GCA GAA AGT AAA GAG-3' (SEQ ID NO: 9)" and "5'-GAA ACA ATA GTA GAC CGA GCA-3' (SEQ ID NO: 10)"; 1c (restriction enzyme HindIII) "5'-GAC CCA TCC GCC GCC TAC TCT-3' (SEQ ID NO: 11)" and "5'-GCA GGT CGT GAA ACA ATC GGT-3' (SEQ ID NO: 12)"; 1d (restriction enzyme HaeIII) "5'-ATT GAG ATG GTA TTG CGG AAG A-3' (SEQ ID NO: 13)" and "5'-CAC ATC GTG CCT TCA AGC TG-3' (SEQ ID NO: 14)"; and 1e (restriction enzyme Sau3AI) "5'-ACA AGG ACG AGG AGG TGG AC-3' (SEQ ID NO: 15)" and "5'-GCT GCT GCT CTT GCT GTT CA-3' (SEQ ID NO: 16)". In addition, one recombinant gene was detected both between 1a (restriction enzyme Sau3AI) "SEQ ID NO: 7" and "SEQ ID NO: 8" and between 1f (restriction enzyme NcoI) "5'-CCA GGA AGT TTG AGA AGA CA-3' (SEQ ID NO: 17)" and "5'-TGC ATT CTG ATG CTT GAT TA-3' (SEQ ID NO: 18)" (FIGS. 1A-1D). Thus, the candidate genome region for the Hd1 gene could be delimited to about 12 kb. Gene prediction and sequence homology search performed on the nucleotide sequence of the candidate region detected a region which shows a high homology to the nucleotide sequence of peroxidase S2539 identified as EST of rice as well as to the *Arahidopsis* CONSTANS (CO)

gene, which have the function to promote flowering under long-day conditions, and has been thought to be a transcriptional regulatory gene having the zinc-finger domain.

EXAMPLE 4

Nucleotide Sequence Analysis of the Hd1 Candidate Gene

S2539, an EST of rice plant, was not altered in the transcript level thereof in RT-PCR performed for Nipponbare and its near-isogenic line of Hd1. Therefore, further analysis was continued using, as an Hd1 candidate gene, a gene predicted to have a zinc-finger domain. To determine the nucleotide sequence of the Hd1 candidate gene of Kasalath, clone No. 47 that carry the candidate gene was selected from a cosmid library constructed from the genomic DNA of Kasalath. Using the cosmid clone thus selected, the nucleotide sequence of the 12-kb Hd1 candidate gene region of Kasalath was determined. Within ORF of the candidate gene region of Kasalath (SEQ ID NO: 19), mutations were found at 11 sites (due to insertion, deletion, and substitution of nucleotides). The largest mutation was represented by a 36-bp insertion and 33-bp deletion within the predicted exon (FIG. 2).

On the other hand, nucleotide sequence analyses of the candidate gene regions were performed for the se1 mutant strains HS66 and HS110. Se1 is presumed to be on the same locus as Hd1, as well as for Ginbozu, the parent strain thereof. The nucleotide sequence was analyzed by cloning the corresponding region using primers that prepared based on the nucleotide sequence of Nipponbare capable of amplifying the Hd1 candidate gene region. As a result, the nucleotide sequence of Ginbozu carrying the Se1 gene was identical with that of Nipponbare except for the 36-bp insertion sequence which was same as that in the sequence of Kasalath and one nucleotide substitution. In the mutant strain HS66 (SEQ ID NO: 20), compared with Ginbozu, a 43-bp deletion was observed in the predicted exon, and, in HS110 (SEQ ID NO: 21), a 433-bp insertion in the intron was detected (FIG. 2).

From the above-described results, the candidate gene having the zinc-finger domain was determined to be a more potential candidate for the Hd1 gene, and a possibility that Se1 locus is the same as Hd1 locus was also suggested.

EXAMPLE 5

Analysis of the Hd1 Candidate Gene Expression Pattern

RT-PCR of the candidate gene was performed for Nipponbare and a near-isogenic line (NIL(Hd1)) thereof in which the Hd1 gene region was substituted with the chromosome fragment of Kasalath. That is, the total RNA was extracted from collected leaves, reverse transcribed to synthesize cDNAs, which were subjected to PCR using a pair of primers containing intron designed in the Hd1 gene: 5'-TTC TCC TCT CCA AAG ATT CC-3' (SEQ ID NO: 22) (sense strand) and 5'-CAT ACG CCT TTC TTG TTT CA-3' (SEQ ID NO: 23) (antisense strand). Assessment of the amount of RNA used as a template was performed by PCR using a pair of primers: 5'-TCC ATC TTG GCA TCT CTC AG-3' (SEQ ID NO: 24) (sense strand) and 5'-GTA CCC GCA TCA GGC ATC TG-3' (SEQ ID NO: 25) (antisense strand), which was capable of amplifying fragments in the actin gene. As a result, the transcript level of the candidate gene of the near-isogenic line derived from Nipponbare having the Kasalath gene at the Hd1 locus noticeably decreased as compared with that of Nipponbare, and the size thereof also slightly became smaller (Table 1).

TABLE 1

| Strain | Duration to the heading[2] | Expression level[3] | Transcript size[2] |
| --- | --- | --- | --- |
| Nipponbare | 111.4 ± 0.55 | +++ | Expected size (Nipponbare) |
| NIL (Hd1)[1] | 96.2 ± 0.84 | + | Slightly smaller |
| Ginbozu | 118.8 ± 0.84 | +++ | Expected size |
| HS66 | 95.2 ± 0.84 | +++ | Slightly smaller |
| HS110 | 99.0 ± 1.00 | + | Mixture of expected size and larger size |

[1]A strain in which the chromosome fragment containing the Hd1 gene region was substituted with the chromosome fragment derived from Kasalath in the genetic background of Nipponbare.
[2]Data in a farm field cultivation (sowing on April 22).
[3]Expression level and size of transcripts of the Hd1 candidate gene were assessed by RT-PCR.

Sizes of transcripts were relative to that which could be amplified in Nipponbare as a standard.

This difference in size was found to correspond to the deletion detected in the genomic nucleotide sequence. Next, a similar analysis of gene expression pattern by RT-PCR was performed for the se1 mutant strains HS66 and HS110 as well as for "Ginbozu", the parent strain thereof. In Ginbozu, a similar transcript to that in Nipponbare was detected. In contrast, in HS66, although the amount of transcript was not different from that of Ginbozu, a slightly smaller transcript was amplified. Extent of decrease in size matched with the 43-bp deletion observed in the genomic nucleotide sequence analysis. On the other hand, in HS110, the uniform size of transcripts was not amplified by RT-PCR, so that transcript of the same size as that of Ginbozu and that of remarkably larger size were amplified (Table 1). These amplified products were cloned and determined the nucleotide sequences thereof, besides the same amplified product as that of Nipponbare, products comprising a part of the 433-bp insertion sequence were then detected. Therefore, these results indicated a possibility that normal splicing was not occurred in HS110 owing to the 433-bp insertion into the intron.

Analysis for relationship between transcripts of the candidate gene and days-to-heading revealed that days-to-heading increased when normal transcripts (in Nipponbare and Ginbozu) were detected, but decreased when aberrant transcripts were found. Furthermore, in HS110, although normal transcript was detected a little, days-to-heading decreased compared with Ginbozu, but slightly increased compared with HS66 (Table 1). These results indicated that HS110 may not be complete loss of function of the Se1.

Putting together the results of analyses of the nucleotide sequence and the results of expression pattern has strongly suggested that the candidate gene corresponds to the Hd1 gene and that the Se1 locus is the same as the Hd1 candidate locus.

EXAMPLE 6

Functional Identification of the Candidate Gene by Transformation

A 7.1-kb ApaI fragment or 3.5-kb HindIII fragment in the genomic region specified as the Hd1 candidate region (FIGS. 1A-1D) was incorporated into the plasmid vector pPZP2H-lac usable for transformation mediated by Agrobacterium, respectively (FIG. 3). Transformation was carried out using the vectors either containing these fragments or not according to the method described by Doi, et al. ((1997) Plant Mol. Biol. Rep. 15: 16-21). As a strain to be transformed, an NIL (Hd1/Hd2) line was used, which has the genetic background of Nipponbare and which lacked the photoperiod sensitivity owing to substitution of the photoperiod sensitivity gene Hd1 and Hd2 of Nipponbare with the gene of Kasalath type. As a result of transformation, 52 hygromycin-resistant individuals were obtained with the vector containing the 7.1-kb fragment, 44 with the vector containing the 3.5-kb fragment, and 19 with the vector alone.

Whether the region to be introduced had indeed been introduced was determined by the PCR method, using a pair of primers specific for the candidate gene: SEQ ID NO: 14 (sense strand) and SEQ ID NO: 15 (antisense strand). As a result, it was indicated that the candidate gene had been integrated into all the recombinants to which 7.1-kb or 3.5-kb fragment was attempted to be introduced.

These individuals were transferred to an isolation greenhouse under the natural long-day conditions (had been transferred from the culture room to isolation greenhouse in mid July, Tsukuba city) as well as to a growth chamber under the short-day conditions (illuminated for 10 hr/day) to score days-to-heading. Under the natural long-day conditions, individuals whose heading was remarkably promoted were appeared in a group of individuals to which the 7.1-kb fragment had been transferred (FIG. 4). Furthermore, in the growth chamber under short-day conditions, a distinct difference in heading dates was observed between individuals containing the 7.1-kb fragment and those with no transgene, where the heading in the former became 7 to 14 days earlier than that in the latter. On the other hand, the heading date of the strain containing the 3.5-kb genomic fragment was about the same as that of individuals containing the vector alone.

From these results, it was confirmed that the candidate gene region (7.1 kb) has the action to promote the heading under short-day conditions. Considering from the fact that heading is promoted under short-day conditions when the plant is highly photoperiod sensitivity, sensitivity in general, the introduced genomic fragment has been proved to have a function to enhance the photoperiod sensitivity.

Furthermore, one individual assumed to carry a single copy of the transgene was selected from a group of individuals whose heading was promoted under short-day conditions, and self-fertilized progenies thereof were similarly cultivated under short-day conditions (illuminated for 10 hr and left in the dark for 14 hr/day). As a result, large variations in days-to-heading were observed among self-fertilized progenies: three late-ripening individuals were found not to carry the transferred gene, while early-ripening individuals other than the former three individuals carried the transgene (FIG. 5). Based on analysis by PCR, four most early-ripening individuals were thought to be homozygous for the transgene. It was also proved that the introduced candidate gene has the function of the Hd1 gene to promote the heading under short-day conditions.

INDUSTRIAL APPLICABILITY

The present invention provides photoperiod sensitivity genes in rice cultivars. The genes of the present invention confer photoperiod sensitivity to rice plants and may be used to control the heading date of rice Therefore, the genes may be very useful in breeding. The heading date of rice plants can be changed by the use of the genes of the invention. Thus, the genes are particularly useful for breeding rice cultivars adapted to particular locations and seasons. Furthermore, the method to breed rice cultivars using a gene of the present invention is beneficial as compared to conventional methods, in that an object plant can be obtained in a short period with high reliability.

Further, the present invention provides methods for assessing the photoperiod sensitivity of plants. Previously, two to three years of exceeding labor was needed to determine the photoperiod sensitivity of one cultivar according to conventional assessment methods which consist of: crossing object cultivars with tester lines to identify the existence of a specific photoperiod sensitivity gene; and then, determining the existence of the gene by the segregation of the heading date in the progeny of the plants. According to the present method, the photoperiod sensitivity of a plant can be determined by: only (1) harvesting a part of the seedling about 2 weeks after seeding; (2) extracting the DNA thereof; and (3) analyzing the DNA. The degree of photoperiod sensitivity of progenies of plants can be determined prior to crossing, based on the presence or absence of the gene, which is a valuable information for selecting and screening parent plant to be crossed. Furthermore, the presence or absence of the photoperiod sensitivity gene in each selected plant can be easily determined using the methods as described above. Thus, the gene serves also as selection markers.

The invention claimed is:

1. An isolated DNA comprising the nucleotide sequence of SEQ ID NO: 2 or 4.

2. A vector comprising the DNA of claim 1.

3. A plant cell transformed with the vector of claim 2.

4. A plant transformant comprising the plant cell of claim 3.

5. The plant transformant of claim 4, wherein said plant transformant is rice.

6. A progeny or a clone of the plant transformant of claim 4 comprising the nucleotide sequence of SEQ ID NO:2 or 4.

7. A breeding material of a plant that is transformed with a vector that comprises the DNA of claim 1, wherein said breeding material retains the DNA of claim 1.

8. A method for producing a plant, which comprises the following steps of (a) introducing the DNA of claim 1 into a plant cell, and (b) regenerating a plant transformant from the plant cell.

9. A method for delaying the heading time of rice said method comprising introducing and expressing the DNA of claim 1 in rice wherein the heading time of rice expressing the DNA of claim 1 is delayed under long day conditions, as compared to rice that does not express the DNA of claim 1.

10. An isolated host cell transformed with a vector comprising the DNA of claim 1.

* * * * *

UNITED STATES PATENT AND TRADEMARK OFFICE
CERTIFICATE OF CORRECTION

| | |
|---|---|
| PATENT NO. | : 7,253,339 B1 |
| APPLICATION NO. | : 10/129453 |
| DATED | : August 7, 2007 |
| INVENTOR(S) | : Masahiro Yano et al. |

It is certified that error appears in the above-identified patent and that said Letters Patent is hereby corrected as shown below:

Column 17
Line 21 through Column 18, line 11,
"These individuals were transferred to an isolation greenhouse under the natural long-day conditions (had been transferred from the culture room to isolation greenhouse in mid July, Tsukuba city) as well as to a growth chamber under the short-day conditions (illuminated for 10 hr/day) to score days-to-heading. Under the natural long-day conditions, individuals whose heading was remarkably promoted were appeared in a group of individuals to which the 7.1-kb fragment had been transferred (Figure 4). Furthermore, in the growth chamber under short-day conditions, a distinct difference in heading dates was observed between individuals containing the 7.1-kb fragment and those with no transgene, where the heading in the former became 7 to 14 days earlier than that in the latter. On the other hand, the heading date of the strain containing the 3.5-kb genomic fragment was about the same as that of individuals containing the vector alone.

From these results, it was confirmed that the candidate gene region (7.1 kb) has the action to promote the heading under short-day conditions. Considering from the fact that heading is promoted under short-day conditions when the plant is highly photoperiod sensitivity, sensitivity in general, the introduced genomic fragment has been proved to have a function to enhance the photoperiod sensitivity.

Furthermore, one individual assumed to carry a single copy of the transgene was selected from a group of individuals whose heading was promoted under short-day conditions, and self-fertilized progenies thereof were similarly cultivated under short-day conditions (illuminated for 10 hr and left in the dark for 14 hr/day). As a result, large variations in days-to-heading were observed among self-fertilized progenies: three late-ripening individuals were found not to carry the transferred gene, while early-ripening individuals other than the former three individuals carried the transgene (Figure 5). Based on analysis by PCR, four most early-ripening individuals were thought to be homozygous for the transgene. It was also proved that the introduced candidate gene has the function of the *Hd1* gene to promote the heading under short-day conditions."

(Correction continued on page 2)

UNITED STATES PATENT AND TRADEMARK OFFICE
CERTIFICATE OF CORRECTION

| | |
|---|---|
| PATENT NO. | : 7,253,339 B1 |
| APPLICATION NO. | : 10/129453 |
| DATED | : August 7, 2007 |
| INVENTOR(S) | : Masahiro Yano et al. |

It is certified that error appears in the above-identified patent and that said Letters Patent is hereby corrected as shown below:

Column 17
Line 21 through Column 18, line 11, Correction continued:

Should read
--These individuals were transferred to a growth chamber under the short-day conditions (illuminated for 10 hr/day) to score days-to-heading. In the growth chamber under short-day conditions, a distinct difference in heading dates was observed between individuals containing the 7.1-kb fragment and those with no transgene, where the heading in the former became 7 to 14 days earlier than that in the latter. On the other hand, the heading date of the strain containing the 3.5-kg genomic fragment was about the same as that of individuals containing the vector alone (Fig. 4).
    Furthermore, one individual assumed to carry a single copy of the transgene was selected from a group of individuals whose heading was promoted under short-day conditions, and self-fertilized progenies thereof were similarly cultivated under short-day conditions (illuminated for 10 hr and left in the dark for 14 hr/day). As a result, large variations in days-to-heading were observed among self-fertilized progenies: three late-ripening individuals were found not to carry the transferred gene, while early-ripening individuals other than the former three individuals carried the transgene (Figure 5). Based on analysis by PCR, four most early-ripening individuals were thought to be homozygous for the transgene. From these results, it was confirmed that the candidate gene region (7.1 kb) has the action to promote the heading under short-day conditions. Considering from the fact that heading is promoted under short-day conditions when the plant is highly photoperiod sensitive, in general, the introduced genomic fragment has been proved to have a function to enhance the photoperiod sensitivity. It was also proved that the introduced candidate gene has the function of the *Hd1* gene to promote the heading under short-day conditions.--

Signed and Sealed this

Fifteenth Day of April, 2008

JON W. DUDAS
*Director of the United States Patent and Trademark Office*

SEQUENCE LISTING

```
<160> NUMBER OF SEQ ID NOS: 25

<210> SEQ ID NO 1
<211> LENGTH: 456
<212> TYPE: PRT
<213> ORGANISM: Oryza sativa

<400> SEQUENCE: 1

Met Ala Gly Arg Phe Gly Thr Phe Leu Met Tyr Leu His Trp Leu Pro
 1               5                  10                  15

His Thr Gly Ala Pro Ser Lys Lys His Ser Gln Asn Ser Thr Arg Ala
            20                  25                  30

Met Arg Ala Lys Ala Thr Thr Thr Thr Ser Lys Ala Thr Ser Phe Met
```

```
                35                  40                  45
Asn Tyr Asn Phe Gly Gly Asn Val Phe Asp Gln Glu Val Gly Val Gly
 50                  55                  60
Gly Glu Gly Gly Gly Gly Glu Gly Ser Gly Cys Pro Trp Ala Arg
 65                  70                  75                  80
Pro Cys Asp Gly Cys Arg Ala Ala Pro Ser Val Val Tyr Cys Arg Ala
                 85                  90                  95
Asp Ala Ala Tyr Leu Cys Ala Ser Asp Ala Arg Val His Ala Ala
                100                 105                 110
Asn Arg Val Ala Ser Arg His Glu Arg Val Arg Val Cys Glu Ala Cys
                115                 120                 125
Glu Arg Ala Pro Ala Ala Leu Ala Cys Arg Ala Asp Ala Ala Ala Leu
130                 135                 140
Cys Val Ala Cys Asp Val Gln Val His Ser Ala Asn Pro Leu Pro Ala
145                 150                 155                 160
Ile Thr Ile Pro Ala Thr Ser Val Leu Ala Glu Ala Val Val Ala Thr
                165                 170                 175
Ala Thr Val Leu Gly Asp Lys Asp Glu Val Asp Ser Trp Leu Leu
                180                 185                 190
Leu Ser Lys Asp Ser Asp Asn Asn Asn Asn Asn Asn Asn Asn Asp
                195                 200                 205
Asn Asp Asn Asn Asp Asn Asn Ser Asn Ser Ser Asn Asn Gly Met
210                 215                 220
Tyr Phe Gly Glu Val Asp Glu Tyr Phe Asp Leu Val Gly Tyr Asn Ser
225                 230                 235                 240
Tyr Tyr Asp Asn Arg Ile Glu Asn Asn Gln Asp Arg Gln Tyr Gly Met
                245                 250                 255
His Glu Gln Gln Glu Gln Gln Gln Gln Gln Glu Met Gln Lys Glu
                260                 265                 270
Phe Ala Glu Lys Glu Gly Ser Glu Cys Val Val Pro Ser Gln Ile Thr
                275                 280                 285
Met Leu Ser Glu Gln Gln His Ser Gly Tyr Gly Val Val Gly Ala Asp
290                 295                 300
Gln Ala Ala Ser Met Thr Ala Gly Val Ser Ala Tyr Thr Asp Ser Ile
305                 310                 315                 320
Ser Asn Ser Ile Ser Phe Ser Ser Met Glu Ala Gly Ile Val Pro Asp
                325                 330                 335
Ser Thr Val Ile Asp Met Pro Asn Ser Arg Ile Leu Thr Pro Ala Gly
                340                 345                 350
Ala Ile Asn Leu Phe Ser Gly Pro Ser Leu Gln Met Ser Leu His Phe
                355                 360                 365
Ser Ser Met Asp Arg Glu Ala Arg Val Leu Arg Tyr Arg Glu Lys Lys
                370                 375                 380
Lys Ala Arg Lys Phe Glu Lys Thr Ile Arg Tyr Glu Thr Arg Lys Ala
385                 390                 395                 400
Tyr Ala Glu Ala Arg Pro Arg Ile Lys Gly Arg Phe Ala Lys Arg Ser
                405                 410                 415
Asp Val Gln Ile Glu Val Asp Gln Met Phe Ser Thr Ala Ala Leu Ser
                420                 425                 430
Asp Gly Ser Tyr Ala Thr Ser Gly Met Asp Leu Ile Ala Phe Cys Phe
                435                 440                 445
Glu Met Glu His Ser Pro Asn Ile
450                 455
```

<210> SEQ ID NO 2
<211> LENGTH: 4814
<212> TYPE: DNA
<213> ORGANISM: Oryza sativa

<400> SEQUENCE: 2

| | | | | | |
|---|---|---|---|---|---|
| aaagcaaaga | tgaacagagg | tggactgttc | tccttacaaa | tttattgcaa aaaaaaagt | 60 |
| agattctcta | tggagaggca | tatttaacgt | tatagcaggg | ctataataag aaacagatgg | 120 |
| ctcaaagaaa | atgataagca | acaaataacc | cataaaggac | ccatgtcata tatagatagg | 180 |
| ccttgcaaac | aaacaaaaaa | aaggtatgca | aggaaataat | agttccttca gcagttgaga | 240 |
| aatcatataa | cagaagaaaa | aaaacacatt | ggtaataatt | tgacttctcc actagaatag | 300 |
| atatttttgg | atgagggagg | ccggcaaaga | aactatttag | tgacatggca ggccgctttg | 360 |
| gaacttttct | catgtatctg | cactggctac | ctcacaccgg | aggttcgtaa aggcggaacg | 420 |
| gctaaggggg | agtgccaatg | actggcacaa | aaccgcatgc | tttggaatcc cagagaaccc | 480 |
| aaccctccct | ttctcttttg | caaaagaatg | tgcataaaga | gagagaggca gcatcttttcc | 540 |
| tctgctcttt | tttgtttttc | cctttatttg | tacatcatca | cagtggcttc caattctccc | 600 |
| cctttgggct | tagttccatc | taagagatgt | ccattgaatt | gtttagggac aatcctagga | 660 |
| atgcatatgg | gaggattcta | ttgatccctg | taaaatctct | ttagggacag tcctaagtta | 720 |
| aaatggaaca | tgattacgac | aaaagagaat | cagtgtactc | atcactaaaa tgcaaagctt | 780 |
| ttttgcgcaa | aagcgcgatt | gctttggctt | aaaaggtatt | gacatcagtt caggttagat | 840 |
| acttagattt | agctcaaggg | cgccaattct | ccataggacc | cgccaaagtg cacaaaatct | 900 |
| ttatctgaaa | acgacccctc | cattgaggat | tggcatcagg | gggtgagaag agaaacgctg | 960 |
| aagcagcaaa | catccaaagg | caaccacaag | acaggcattg | cagccgccgc tcgccccccc | 1020 |
| cccccccccc | cccgggggatc | gcgccaagtg | tcaatcgctg | gattcgactt gacacccccct | 1080 |
| tactattagt | atactctaca | ctcaaactcc | ccaggacaaa | acaccgtga ctttcccctc | 1140 |
| cctagctcct | tccaaaaaac | actcacaaaa | ttccacaaga | gccatgcgag gtagaggaac | 1200 |
| aggagaagac | gcatacacac | acgacacata | gagagagagg | acaaacacaa tagcttggat | 1260 |
| cgatagactt | gtccatgtgg | tgcaagctaa | agctactact | accacaagca aggctacttc | 1320 |
| gttcatgaat | tataattttg | gtggcaacgt | gttcgaccag | gaggttggag ttggaggcga | 1380 |
| aggaggagga | ggaggagagg | ggagcggctg | cccatgggcg | cggccgtgcg acgggtgccg | 1440 |
| cgcggcgccg | agcgtggtgt | actgccgcgc | ggacgcggcg | tacctgtgcg cgtcgtgcga | 1500 |
| cgcgcgggtg | cacgcggcca | accgcgtggc | gtcccgccac | gagcgcgtgc gggtgtgcga | 1560 |
| ggcctgcgag | cgcgccccgg | ccgcgctcgc | gtgccgcgcc | gacgccgccg cgctgtgcgt | 1620 |
| ggcgtgcgac | gtgcaggtgc | actccgcgaa | cccgctcccg | gccatcacca tcccggccac | 1680 |
| ctccgtcctc | gctgaggcgg | tggtggccac | cgccaccgtc | ctcggcgaca aggacgagga | 1740 |
| ggtggactct | tggcttctcc | tctccaaaga | ttccgacaac | acaacaacaa ataacaacaa | 1800 |
| caacgacaac | gacaataacg | acaacaacaa | cagcaacagc | agcaacaacg gcatgtattt | 1860 |
| tggtgaagtc | gatgagtact | ttgatcttgt | cgggtacaat | tcgtactacg acaaccgcat | 1920 |
| cgaaaacaac | caagatcggc | agtatgggat | gcatgaacag | caagagcagc agcagcagca | 1980 |
| gcaggagatg | caaaaggagt | ttgcagagaa | ggaagggagc | gagtgtgtgg taccttcaca | 2040 |
| gatcacaatg | ctgagtgagc | agcagcatag | tggttatgga | gttgtgggag cagaccaggc | 2100 |

-continued

| | | | | |
|---|---|---|---|---|
| cgcctccatg | accgccggcg | tcagtgctta | cacagattcc | atcagcaaca | gcgtgagttc | 2160 |
| atctattact | agctgcaact | atttttttt | cagagaatga | acatctatta | ctgttgttag | 2220 |
| ttagttgtta | ctacatgcca | cgttgtcaat | gttttagagt | tcatactagt | acttttgagt | 2280 |
| ggaaaaacat | tctccaaaca | aaagctactg | tctaacaaaa | tgaagggata | aataaacaga | 2340 |
| tctcaacaag | aaaacaaaga | tacttttcta | cttccaagct | gcgatcttta | ggctgattaa | 2400 |
| atggaaccga | taaaaaaaat | actttaaaga | aaagtacaca | attgatcttt | aggcagacca | 2460 |
| gttgactact | tcctgtattt | ctaagcatat | acgatccatg | ctaactcact | aattgaaaag | 2520 |
| aagtgagttt | gttaaccttt | tatgtacaca | gcaatcacca | cacgaaagac | ctcatgaaaa | 2580 |
| gtaggataag | tgtaagtgta | attcatattt | tatcccagtg | cataaattta | aaatatctta | 2640 |
| cttttgcgac | agtaaaaaag | atattggaag | tttttcttat | gtatgtaaaa | ttaaattaag | 2700 |
| cccatctata | tatcattgca | gggtctctga | cacctgcaat | ctccttatga | ttcgcatatt | 2760 |
| tcagtgacca | tttgccgatt | ccatctcaga | tatctttctc | atcaatggag | gcgggtatag | 2820 |
| taccagacag | cacggtgata | gatatgccaa | attccagaat | cctgacacct | gctggagcaa | 2880 |
| tcaatctctt | ctcaggtccc | tcgcttcaga | tgtcccttca | cttcagctcc | atggacaggg | 2940 |
| aggccagggt | gctcaggtac | agggagaaga | agaaggccag | gaagtttgag | aagacaatac | 3000 |
| gttatgaaac | aagaaaggcg | tatgcagagg | cacgaccccg | gatcaagggc | cgtttcgcca | 3060 |
| agagatcaga | tgtgcagatc | gaagtggacc | agatgttctc | cactgcagct | ctatctgacg | 3120 |
| gtagctatgg | tactgttcca | tggttctgat | gggactcatg | agacgctatc | ttataggcat | 3180 |
| atatatgggg | acttactgag | tagcaataac | atcgatccag | tgggagtagt | tctagacaat | 3240 |
| ctgtgttatg | aataatagtg | tgttgtttgc | gacttaaaat | tgatcaagta | ccttagcttt | 3300 |
| ttaaagttttt | gctttgtaat | ttccggatag | cagatatata | ttgttggtac | ttgctcagta | 3360 |
| gctttaagtt | tttgaagtaa | gcaaagagca | gtgatgagat | gaaatgagta | tgtgtataac | 3420 |
| tgtatataga | taattctagg | gtaccttggc | caacaatcac | agtagcaaca | atgctttagg | 3480 |
| ggtttaggtg | acgaattggg | ggtttagttg | tttactatga | agtagcacca | aaatggtgga | 3540 |
| acatatatat | tcctattttc | gttccatcat | gacatataac | tgctgtctaa | ccagcctatg | 3600 |
| ttgactgaaa | acaaagctcg | tttcattaca | aaataaaaga | tggaaccctg | attaagtgtg | 3660 |
| tccactggcc | agatagtatc | atagtagtat | aataatgaac | tggagttcaa | gtctttttata | 3720 |
| ttccacttgg | atctcggtgc | cattttctta | atgatgtatc | ttagtgatgg | gctatcattg | 3780 |
| tatccggttg | gaatttcagc | agaggtgaag | gtgatggtgt | tcactcagct | tttaaatatc | 3840 |
| cattattctt | acagccctcc | agatcattct | ggatgaaaag | aaaagcagtg | acaaagaatt | 3900 |
| tactgttgct | ttaaccatga | gaatcatatc | tttccagcac | ggcctatctt | ctcactaaac | 3960 |
| catgagctat | cggtgatcag | taactcgaat | gatagttgta | gggaatatag | gaacattgcc | 4020 |
| tgatactgat | aggtacacca | ttgtggttgg | gtgatataag | tacaacaaac | tcacagaaaa | 4080 |
| gtttccctat | tattttgtga | atcaagagag | cataaataag | gaagctcttt | ctcattctca | 4140 |
| gtgcattcct | cttcccttc | actagcaact | agtggcatgg | atcttattgc | cttttgtttt | 4200 |
| gagatggagc | attcaccaaa | tatctaaggc | atctcagggc | accaaccgca | tatacaggaa | 4260 |
| tacaggatac | atctaatcgt | ttttggctaa | gcttgactgt | atcggttaga | tattgcacaa | 4320 |
| aaaacagagt | taggaattaa | gccctaagag | atggtaattg | gaaactggaa | agtgaacttt | 4380 |
| tcatttcaaa | tatcaacaaa | gagaggtcaa | aaaagtaaag | tgaaataaag | cacacgggag | 4440 |
| atacagatcc | atattttgac | cgaaactgac | gacatatacc | actctagtat | ggatagagag | 4500 |

```
aacaaatcaa agttctgcag aagataaaac tagacatagt tgactagtaa cagaagagat    4560
tcctgaactt tctcactgaa actatcaagc aaatagataa aactcgtggt gatatttcat    4620
ccacatcagc actgagaaca gaacagcaag caagcagttt gattgtgatg gagggagctc    4680
ctagcacatc atcatattat gaagtaatat ttaataatca tggaagtatg atgaaggtat    4740
ttttctggca acagttcttg tttgatgcat cagaatacct gattaacgtg gaattaatca    4800
agcatcagaa tcca                                                      4814

<210> SEQ ID NO 3
<211> LENGTH: 468
<212> TYPE: PRT
<213> ORGANISM: Oryza sativa

<400> SEQUENCE: 3

Met Ala Gly Arg Phe Gly Thr Phe Leu Met Tyr Leu His Trp Leu Pro
 1               5                  10                  15

His Thr Gly Ala Pro Ser Lys Lys His Ser Gln Asn Ser Thr Arg Ala
            20                  25                  30

Met Arg Ala Lys Ala Thr Thr Thr Thr Ser Lys Ala Thr Ser Phe Met
        35                  40                  45

Asn Tyr Asn Phe Gly Gly Asn Val Phe Asp Gln Glu Val Gly Val Gly
    50                  55                  60

Gly Glu Gly Gly Gly Gly Glu Gly Ser Gly Cys Pro Trp Ala Arg
65                  70                  75                  80

Pro Cys Asp Gly Cys Arg Ala Ala Pro Ser Val Val Tyr Cys Arg Ala
                85                  90                  95

Asp Ala Ala Tyr Leu Cys Ala Ser Cys Asp Ala Arg Val His Ala Ala
            100                 105                 110

Asn Arg Val Ala Ser Arg His Glu Arg Val Arg Val Cys Glu Ala Cys
        115                 120                 125

Glu Arg Ala Pro Ala Ala Leu Ala Cys Arg Ala Asp Ala Ala Ala Leu
    130                 135                 140

Cys Val Ala Cys Asp Val Gln Val Tyr Ser Ala Asn Pro Leu Ala Arg
145                 150                 155                 160

Arg His Gln Arg Val Pro Val Ala Pro Leu Pro Ala Ile Thr Ile Pro
                165                 170                 175

Ala Thr Ser Val Leu Ala Glu Ala Val Val Ala Thr Ala Thr Val Leu
            180                 185                 190

Gly Asp Lys Asp Glu Glu Val Asp Ser Trp Leu Leu Leu Ser Lys Asp
        195                 200                 205

Ser Asp Asn Asn Asn Asn Asn Asn Asn Asp Asn Asp Asn Asn
    210                 215                 220

Asp Asn Asn Asn Ser Asn Ser Ser Asn Asn Gly Met Tyr Phe Gly Glu
225                 230                 235                 240

Val Asp Glu Tyr Phe Asp Leu Val Gly Tyr Asn Ser Tyr Tyr Asp Asn
                245                 250                 255

Arg Ile Glu Asn Asn Gln Asp Arg Gln Tyr Gly Met His Glu Gln Gln
            260                 265                 270

Glu Gln Gln Gln Gln Gln Glu Met Gln Lys Glu Phe Ala Glu Lys
        275                 280                 285

Glu Gly Ser Glu Cys Val Val Pro Ser Gln Ile Thr Met Leu Ser Glu
    290                 295                 300

Gln Gln His Ser Gly Tyr Gly Val Val Gly Ala Asp Gln Ala Ala Ser
```

```
                305                 310                 315                 320
Met Thr Ala Gly Val Ser Ala Tyr Thr Asp Ser Ile Ser Asn Ser Ile
                    325                 330                 335

Ser Phe Ser Ser Met Glu Ala Gly Ile Val Pro Asp Ser Thr Val Ile
                340                 345                 350

Asp Met Pro Asn Ser Arg Ile Leu Thr Pro Ala Gly Ala Ile Asn Leu
            355                 360                 365

Phe Ser Gly Pro Ser Leu Gln Met Ser Leu His Phe Ser Ser Met Asp
        370                 375                 380

Arg Glu Ala Arg Val Leu Arg Tyr Arg Glu Lys Lys Ala Arg Lys
385                 390                 395                 400

Phe Glu Lys Thr Ile Arg Tyr Glu Thr Arg Lys Ala Tyr Ala Glu Ala
                405                 410                 415

Arg Pro Arg Ile Lys Gly Arg Phe Ala Lys Arg Ser Asp Val Gln Ile
            420                 425                 430

Glu Val Asp Gln Met Phe Ser Thr Ala Ala Leu Ser Asp Gly Ser Tyr
        435                 440                 445

Ala Thr Ser Gly Met Asp Leu Ile Ala Phe Cys Phe Glu Met Glu His
    450                 455                 460

Ser Pro Asn Ile
465

<210> SEQ ID NO 4
<211> LENGTH: 4850
<212> TYPE: DNA
<213> ORGANISM: Oryza sativa

<400> SEQUENCE: 4
aaagcaaaga tgaacagagg tggactgttc tccttacaaa tttattgcaa aaaaaaagt      60
agattctcta tggagaggca tatttaacgt tatagcaggg ctataataag aaacagatgg    120
ctcaaagaaa atgataagca acaaataacc cataaaggac ccatgtcata tatagatagg    180
ccttgcaaac aaacaaaaaa aaggtatgca aggaaataat agttccttca gcagttgaga    240
aatcatataa cagaagaaaa aaaacacatt ggtaataatt tgacttctcc actagaatag    300
atattttggg atgagggagg ccggcaaaga aactatttag tgacatggca ggccgctttg    360
gaacttttct catgtatctg cactggctac ctcacaccgg aggttcgtaa aggcggaacg    420
gctaaggggg agtgccaatg actggcacaa accgcatgc tttggaatcc agagaaccc     480
aaccctccct ttctcttttg caaaagaatg tgcataaaga gagagaggca gcatctttcc    540
tctgctcttt tttgtttttc cctttatttg tacatcatca cagtggcttc caattctccc    600
cctttgggct tagttccatc taagagatgt ccattgaatt gtttagggac aatcctagga    660
atgcatatgg gaggattcta ttgatccctg taaaatctct ttagggacag tcctaagtta    720
aaatggaaca tgattacgac aaaagagaat cagtgtactc atcactaaaa tgcaaagctt    780
ttttgcgcaa aagcgcgatt gctttggctt aaaaggtatt gacatcagtt caggttagat    840
acttagattt agctcaaggg cgccaattct ccataggacc cgccaaagtg cacaaaatct    900
ttatctgaaa acgacccctc cattgaggat tggcatcagg gggtgagaag agaaacgctg    960
aagcagcaaa catccaaagg caaccacaag acaggcattg cagccgccgc tcgcccccc    1020
cccccccc ccgggggatc gcgccaagtg tcaatcgctg gattcgactt gacaccccct     1080
tactattagt atactctaca ctcaaactcc ccaggacaaa acaccgtga ctttcccctc    1140
cctagctcct tccaaaaaac actcacaaaa ttccacaaga gccatgcgag gtagaggaac    1200
```

```
aggagaagac gcatacacac acgacacata gagagagagg acaaacacaa tagcttggat    1260
cgatagactt gtccatgtgg tgcaagctaa agctactact accacaagca aggctacttc    1320
gttcatgaat tataattttg gtggcaacgt gttcgaccag gaggttggag ttggaggcga    1380
aggaggagga ggaggagagg ggagcggctg cccatgggcg cggccgtgcg acgggtgccg    1440
cgcggcgccg agcgtggtgt actgccgcgc ggacgcggcg tacctgtgcg cgtcgtgcga    1500
cgcgcgggtg cacgcggcca accgcgtggc gtcccgccac gagcgcgtgc gggtgtgcga    1560
ggcctgcgag cgcgccccgg ccgcgctcgc gtgccgcgcc gacgccgccg cgctgtgcgt    1620
ggcgtgcgac gtgcaggtgt actccgcgaa cccgctcgcc aggcgccacc agcgcgtccc    1680
cgtcgcgccg ctcccggcca tcaccatccc ggccacctcc gtcctcgctg aggcggtggt    1740
ggccaccgcc accgtcctcg cgacaagga cgaggaggtg gactcttggc ttctcctctc    1800
caaagattcc gacaacaaca acaacaataa caacaacaac gacaacgaca ataacgacaa    1860
caacaacagc aacagcagca caacggcat gtattttggt gaagtcgatg agtactttga    1920
tcttgtcggg tacaattcgt actacgacaa ccgcatcgaa aacaaccaag atcggcagta    1980
tgggatgcat gaacagcaag agcagcagca gcagcagcag gagatgcaaa aggagtttgc    2040
agagaaggaa gggagcgagt gtgtggtacc ttcacagatc acaatgctga gtgagcagca    2100
gcatagtggt tatggagttg tgggagcaga ccaggccgcc tccatgaccg ccggcgtcag    2160
tgcttacaca gattccatca gcaacagcgt gagttcatct attactagct gcaactattt    2220
ttttttcaga gaatgaacat ctattactgt tgttagttag ttgttactac atgccacgtt    2280
gtcaatgttt tagagttcat actagtactt ttgagtggaa aaacattctc caaacaaaag    2340
ctactgtcta acaaaatgaa gggataaata aacagatctc aacaagaaaa caagatact    2400 tttctacttc caagctgcga tctttaggct gattaaatgg aaccgataaa aaaatactt    2460 taaagaaaag tacacaattg atctttaggc agaccagttg actacttcct gtatttctaa    2520
gcatatacga tccatgctaa ctcactaatt gaaagaagt gagtttgtta acctttatg    2580 tacacagcaa tcaccacacg aaagacctca tgaaaagtag gataagtgta agtgtaattc    2640
atattttatc ccagtgcata aatttaaaat atcttacttt tgcgacagta aaaagatat    2700 tggaagtttt tcttatgtat gtaaaattaa attaagccca tctatatatc attgcagggt    2760
ctctgacacc tgcaatctcc ttatgattcg catatttcag tgaccatttg ccgattccat    2820
ctcagatatc tttctcatca atggaggcgg gtatagtacc agacagcacg gtgatagata    2880
tgccaaattc cagaatcctg acacctgctg gagcaatcaa tctcttctca ggtccctcgc    2940
ttcagatgtc ccttcacttc agctccatgg cagggaggc cagggtgctc aggtacaggg    3000
agaagaagaa ggccaggaag tttgagaaga caatacgtta tgaaacaaga aaggcgtatg    3060
cagaggcacg accccggatc aagggccgtt tcgccaagag atcagatgtg cagatcgaag    3120
tggaccagat gttctccact gcagctctat ctgacggtag ctatggtact gttccatggt    3180
tctgatggga ctcatgagac gctatctttat aggcatatat atgggacttt actgagtagc    3240
aataacatcg atccagtggg agtagttcta gacaatctgt gttatgaata atagtgtgtt    3300
gtttgcgact taaaattgat caagtacctt agcttttaa agttttgctt tgtaatttcc    3360
ggatagcaga tatatattgt tggtacttgc tcagtagctt taagtttttg aagtaagcaa    3420
agagcagtga tgagatgaaa tgagtatgtg tataactgta tatagataat tctagggtac    3480
cttggccaac aatcacagta gcaacaatgc tttagggggtt taggtgacga attgggggtt    3540
```

-continued

```
tagttgttta ctatgaagta gcaccaaaat ggtggaacat atatattcct attttcgttc    3600
catcatgaca tataactgct gtctaaccag cctatgttga ctgaaaacaa agctcgtttc    3660
attacaaaat aaaagatgga accctgatta agtgtgtcca ctggccagat agtatcatag    3720
tagtataata atgaactgga gttcaagtct tttatattcc acttggatct cggtgccatt    3780
ttcttaatga tgtatcttag tgatgggcta tcattgtatc cggttggaat ttcagcagag    3840
gtgaaggtga tggtgttcac tcagctttta aatatccatt attcttacag ccctccagat    3900
cattctggat gaaagaaaa gcagtgacaa agaatttact gttgctttaa ccatgagaat     3960
catatctttc cagcacggcc tatcttctca ctaaaccatg agctatcggt gatcagtaac    4020
tcgaatgata gttgtaggga atataggaac attgcctgat actgataggt acaccattgt    4080
ggttgggtga tataagtaca acaaactcac agaaaagttt ccctattatt ttgtgaatca    4140
agagagcata aataaggaag ctctttctca ttctcagtgc attcctcttc cctttcacta    4200
gcaactagtg gcatggatct tattgccttt tgttttgaga tggagcattc accaaatatc    4260
taaggcatct cagggcacca accgcatata caggaataca ggatacatct aatcgttttt    4320
ggctaagctt gactgtatcg gttagatatt gcacaaaaaa cagagttagg aattaagccc    4380
taagagatgg taattggaaa ctggaaagtg aactttttcat ttcaaatatc aacaaagaga   4440
ggtcaaaaaa gtaaagtgaa ataaagcaca cgggagatac agatccatat tttgaccgaa    4500
actgacgaca tataccactc tagtatggat agagagaaca aatcaaagtt ctgcagaaga    4560
taaaactaga catagttgac tagtaacaga agagattcct gaactttctc actgaaacta    4620
tcaagcaaat agataaaact cgtggtgata tttcatccac atcagcactg agaacagaac    4680
agcaagcaag cagtttgatt gtgatggagg gagctcctag cacatcatca tattatgaag    4740
taatatttaa taatcatgga agtatgatga aggtattttt ctggcaacag ttcttgtttg    4800
atgcatcaga atacctgatt aacgtggaat taatcaagca tcagaatcca              4850
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:Artificially Synthesized Primer Sequence

<400> SEQUENCE: 5
ggactgggtg aagaagat                                                  18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:Artificially Synthesized Primer Sequence

<400> SEQUENCE: 6
ccttgtcctc tcctcttg                                                  18

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:Artificially Synthesized Primer Sequence -continued

```
<400> SEQUENCE: 7
gtagagtgat gacaaaatga caa                                               23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
ggactgagat ggaatgtgct                                                   20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
aagcaagcag aaagtaaaga g                                                 21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
gaaacaatag tagaccgagc a                                                 21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
gacccatccg ccgcctactc t                                                 21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
gcaggtcgtg aaacaatcgg t                                                 21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
```

```
attgagatgg tattgcggaa ga                                               22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
cacatcgtgc cttcaagctg                                                  20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 15
acaaggacga ggaggtggac                                                  20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 16
gctgctgctc ttgctgttca                                                  20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 17
ccaggaagtt tgagaagaca                                                  20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 18
tgcattctga tgcttgatta                                                  20

<210> SEQ ID NO 19
<211> LENGTH: 4810
<212> TYPE: DNA
<213> ORGANISM: Oryza sativa

<400> SEQUENCE: 19
aaagcaaaga tgaacagagg tggactgttc tccttacaaa tttattgcaa aaaaaaaag       60 tagattctct atggagaggc atatttaacg ttatagcagg gctataataa gaaccagatg     120
```

-continued

```
gctcaaagaa aatgataagc aacaaataac ccataaagga cccatgtcat atatagatag      180
gccttgcaaa caaacaaaaa aaaggtatgc aaggaaataa tagttccttc agcagttgag      240
aaatcatata acagaagaaa aaaaacacat tggtaataat ttgacttctc cactagaata      300 gatattttg gatgagggag gccggcaaag aaactattta gtgacatggc aggccgcttt       360
ggaacttttc tcatgtatct gcactggcta cctcacaccg gaggttcgta aaggcggaac      420
ggctaagggg gagtgccaat gactggcaca aaaccgcatg ctttggaatc cagagaacc      480 caaccctccc tttctctttt gcaaaagaat gtgcataaag agagagaggc agcatatttc      540
ctctgctctt ttttgttttt ccctttattt gtacatcatc acagtggctt ccaattctcc      600
ccctttgggc ttagttccat ctaagagatg tccattgaat tgtttaggga caatcctagg      660
aatgcatatg ggaggattct attgatccct gtaaaatctc tttagggaca gtcctaagtt      720
aaaatggaac atgattacga caaaagagaa tcagtgtact catcactaaa atgcaaagct      780
tttttgcgca aaagcgcgat tgctttggct taaaaggtat tgacatcagt tcaggttaga      840
tacttagatt tagctcaagg gcgccaattc tccataggac ccgccaaagt gcacaaaatc      900
tttatctgaa aacgacccct ccattgagga ttggcatcag ggggtgagaa gagaaacgct      960
gaagcagaaa acatccaaag gcaaccacaa gacaggcatt gcagccgccg ttccccccc      1020 cccccccccg gggatcgcgc caagtgtcac tcgctggatt cgacttgaca cccccttact      1080
attagtatac tctacagtca aactccccag gacaaaaaca ccgtgacttt ccctccccta     1140
gctccttcca aaaacactc acaaaattcc acaagagcca tgcgaggtag aggaacagga     1200
gaagacgcat acacacacga cacatagaga gagaggacaa acacaatagc ttggatcgat     1260
agacttgtcc atgtggtgca agctaaagct actactacca caagcaaggc tacttcgttc     1320
atgaattata atttggtgg caacgtgttc gaccaggagg ttggagttgg aggcgaagga     1380
ggaggaggag gagaggggag cggctgccca tgggcgcggc cgtgcgacgg gtgccgcgcg     1440
gcgccgagcg tggtgtactg ccgcgcggac gcggcgtacc tgtgcgcgtc gtgcgacgcg     1500
cgggtgcacg cggccaaccg cgtggcgtcc cgccacgagc gcgtgcgggt gtgcgaggcc     1560
tgcgagcaag ccccggccgc gctcgcgtgc cgcgccgacg ccgccgcgct gtgcgtggcg     1620
tgcgacgtgc aggtgcactc cgcgaacccg ctcgccaggc gccaccagcg cgtccccgtc     1680
gcgccgctcc cggccatcac catcccggcc acctccgtcc tcgctgaggc ggtggtggcc     1740
accgccaccg tcctcggcgg caaggacgag gaggtggact cttggattat cctctccaaa     1800
gattccaaca acaacaacaa caataacaac agcaacagca gcaacaacgg catgtatttt     1860
ggtgaagtcg atgagtactt tgatcttgtc gggtacaatt cgtactacga caaccgcatc     1920
gaaaacaacc aagatcagca gtatgggatg catgaacagc aagagcagca gcagcagcag     1980
caggagatgc aaaaggagtt tgcagagaag gaagggagcg agtgtgtggt accttcacag     2040
atcacaatgc tgagtgagca gcagcatagt ggttatgag ttgtgggagc agaccaggcc      2100
gcctccatga ccgccggcgt cagtgcttac acagattcca tcagcaacag cgtgagttca     2160
tctattacta gctgcaacta ttttttttc agagaatgaa catctattac tgttgttagt      2220
tagttgttac tacatgccac gttgtcaatg ttttagagtt catactagta cttttagtg      2280 gaaaaacatt ctccaaacaa aagctactgt ctaacaaaat gaaggataa ataaacagat      2340 ctcaacaaga aaataagat acttttctac ttccaagctg cgatctttag gctgattaaa     2400
tggaaccgat aaaaaaata ctttaaagaa agtacacaat tgatctttag gcagaccagt     2460
```

```
tgactagttc ctgtatttct aagcatatac catccatgct aactcactaa ttgaaaagaa    2520
gtgagtttgt taaccttta tgtacacagc aatcaccaca cgaaagacct catgaaaagt    2580
aggataagtg taagtgtaat tcatatttta tcccagtgca taaatttaaa atatcttact    2640
tttgcgacag taaaaaagat attggaagtt tttcttatgt atgtaaaatt aaattaagcc    2700
catctatata tcattgcagg gtctctgaca cctgcaatct ccttatgatt cgcatatttc    2760
agtgaccatt tgccgattcc atctcagata tctctcatca atggaggcgg gtatagtacc    2820
agacagcacg gtgatagata tgccaaattc cagcatcctg acacctgctg gagcaatcaa    2880
tctcttctca ggtccctcgc ttcagatgtc ccttcacttc agctccatgg acagggaggc    2940
cagggtgctc aggtacaggg agaagaagaa ggccaggaag tttgagaaga caatacgtta    3000
tgaaacaaga aaggcgtatg cagaggcacg accccggatc aagggccgtt tcgccaagag    3060
atcagatgtg cagatcgaag tggaccagat gttctccact gcagctctat ctgacagtag    3120
ctatggtact gttccatggt tctgatggga ctcatgagac gctatcttat aggcatatat    3180
atggggactt actgagtagc aataacatcg atccagtggg agtagttcta gacaatctgt    3240
gttatgaata atagtgtgtt gtttgcgact taaaattgat caagtacctt agcttttttaa   3300 agttttgctt tgtaatttcc ggatagcaga tatatattgt tggtacttgc tcagtagctt    3360 taagttttg aagtaagcaa agagcagtga tgagatgaaa tgagtatgtg tataactgta    3420
tatagataat tctagggtac cttggccaac aatcacagta gcaacaatgc tttaggggtt    3480
taggtgacga attgggggtt tagttgttta ctatgaagta gcaccaaaat ggtggaacat    3540
atatattcct attttcgttc catcatgaca tataactgct gtctaaccag cctatgttga    3600
ctgaaaacaa agctcgtttc attacaaaat aaaagatgga accctgatta agtgtgtcca    3660
ctggccagat agtatcatag tagtataata atgaactgga gttcaagtct tttatattcc    3720
acttggatct cggtgccatt tcttaatga tgtatcttag tgatgggcta tcattgtatc    3780
cggttggaat tcagcagag gtgaaggtga tggtgttcac tcagctttta aatatccatt    3840
attcttacag ccctccagat cattctggat gaaaagaaaa gcagtgacaa agaatttact    3900
gttgctttaa ccatgagaat catatctttc cagcacggcc tatcttctca ctaaaccatg    3960
ggctatcggt gatcagtaac tcgaatgata gttgtaggga atataggaac attgcctgat    4020
actgataggt acaccattgt ggttgggtga tataagtaca acaaactcac agaaaagttt    4080
ccctattatt ttgtgaatca agagagcata aataaggaag ctctttctca ttctcagtgc    4140
attcctcttc cctctcacta gcaactagtg gcatggatct tattgccttt tgttttgaga    4200
tggagcattc accaaatatc taaggcatct cagggcacca accgcatata caggaataca    4260
ggatacatct aatcgttttt ggctaagctt gactgtatcg gttagatatt gcacaaaaaa    4320
cagagttagg aattaagccc taagagatgg taattggaaa ctggaaagtg aacttttcat    4380
ttcaaatatc aacaaagaga ggtcaaaaaa gtaaagtgaa ataaagcaca cgggagatac    4440
agatccatat tttgaccgaa actgacgaca tataccactc tagtatggat agagagaaca    4500
aatcaaagtt ctgcagaaga taaaactaga catagttgac tagtaacaga agagattcct    4560 gaacttctc actgaaacta tcaagcaaat agataaaact cgtggtgata tttcatccac    4620
atcagcactg agaacagaac agcaagcaag cagtttgatt gtgatggagg gagctcctag    4680
cacatcatca tattatgaag taatattaa taatcatgga agtatgatga aggtattttt    4740
ctggcaacag ttcttgtttg atgcatcaga atacctgatt agcgtggaat taatcaagca    4800
tcagaatcca                                                          4810
```

<210> SEQ ID NO 20
<211> LENGTH: 4807
<212> TYPE: DNA
<213> ORGANISM: Oryza sativa

<400> SEQUENCE: 20

| | | | | | |
|---|---|---|---|---|---|
| aaagcaaaga | tgaacagagg | tggactgttc | tccttacaaa | tttattgcaa | aaaaaaagt 60 |
| agattctcta | tggagaggca | tatttaacgt | tatagcaggg | ctataataag | aaacagatgg 120 |
| ctcaaagaaa | atgataagca | acaaataacc | cataaaggac | ccatgtcata | tatagatagg 180 |
| ccttgcaaac | aaacaaaaaa | aaggtatgca | aggaaataat | agttccttca | gcagttgaga 240 |
| aatcatataa | cagaagaaaa | aaaacacatt | ggtaataatt | tgacttctcc | actagaatag 300 |
| atattttggg | atgagggagg | ccggcaaaga | aactatttag | tgacatggca | ggccgctttg 360 |
| gaacttttct | catgtatctg | cactggctac | ctcacaccgg | aggttcgtaa | aggcggaacg 420 |
| gctaaggggg | agtgccaatg | actggcacaa | aaccgcatgc | tttggaatcc | cagagaaccc 480 |
| aaccctccct | ttctcttttg | caaagaatg | tgcataaaga | gagagaggca | gcatcttttcc 540 |
| tctgctcttt | tttgtttttc | cctttatttg | tacatcatca | cagtggcttc | caattctccc 600 |
| cctttgggct | tagttccatc | taagagatgt | ccattgaatt | gtttagggac | aatcctagga 660 |
| atgcatatgg | gaggattcta | ttgatccctg | taaaatctct | ttagggacag | tcctaagtta 720 |
| aaatggaaca | tgattacgac | aaaagagaat | cagtgtactc | atcactaaaa | tgcaaagctt 780 |
| ttttgcgcaa | aagcgcgatt | gctttggctt | aaaaggtatt | gacatcagtt | caggttagat 840 |
| acttagattt | agctcaaggg | cgccaattct | ccataggacc | cgccaaagtg | cacaaaatct 900 |
| ttatctgaaa | acgacccctc | cattgaggat | tggcatcagg | gggtgagaag | agaaacgctg 960 |
| aagcagcaaa | catccaaagg | caaccacaag | acaggcattg | cagccgccgc | tcgcccccccc 1020 |
| cccccccccc | cccgggatc | gcgccaagtg | tcaatcgctg | gattcgactt | gacacccct 1080 |
| tactattagt | atactctaca | ctcaaactcc | ccaggacaaa | acaccgtga | ctttccctc 1140 |
| cctagctcct | tccaaaaaac | actcacaaaa | ttccacaaga | gccatgcgag | gtagaggaac 1200 |
| aggagaagac | gcatacacac | acgacacata | gagagagagg | acaaacacaa | tagcttggat 1260 |
| cgatagactt | gtccatgtgg | tgcaagctaa | agctactact | accacaagca | aggctacttc 1320 |
| gttcatgaat | tataattttg | gtggcaacgt | gttcgaccag | gaggttggag | ttggaggcga 1380 |
| aggaggagga | ggaggagagg | ggagcggctg | cccatgggcg | cggccgtgcg | acgggtgccg 1440 |
| cgcggcgccg | agcgtggtgt | actgccgcgc | ggacgcggcg | tacctgtgcg | cgtcgtgcga 1500 |
| cgcgcgggtg | cacgcggcca | accgcgtggc | gtcccgccac | gagcgcgtgc | gggtgtgcga 1560 |
| ggcctgcgag | cgcgccccgg | ccgcgctcgc | gtgccgcgcc | gacgccgccg | cgctgtgcgt 1620 |
| ggcgtgcgac | gtgcaggtgt | actccgcgaa | cccgctcgcc | aggcgccacc | agcgcgtccc 1680 |
| cgtcgcgccg | ctcccggcca | tcaccatccc | ggccacctcc | gtcctcgctg | aggcggtggt 1740 |
| ggccaccgcc | accgtcctcg | cgacaagga | cgaggaggtg | gactcttggc | ttctcctctc 1800 |
| caaagattcc | gacaacaaca | acaacaataa | caacaacaac | gacaacgaca | ataacgacaa 1860 |
| caacaacagc | aacagcagca | acaacggcat | gtattttggt | gaagtcgatg | agtactttga 1920 |
| tcttgtcggg | tacaattcgt | actacgacaa | ccgcatcgaa | acaaccaag | atcggcagta 1980 |
| tgggatgcat | gaacagcaag | agcagcagca | gcagcagcag | gagatgcaaa | aggagtttgc 2040 |
| agagaaggaa | gggagcgagt | gtgtggttat | ggagttgtgg | gagcagacca | ggccgcctcc 2100 |

-continued

```
atgaccgccg gcgtcagtgc ttacacagat tccatcagca acagcgtgag ttcatctatt       2160
actagctgca actatttttt tttcagagaa tgaacatcta ttactgttgt tagttagttg       2220
ttactacatg ccacgttgtc aatgttttag agttcatact agtacttttg agtggaaaaa       2280
cattctccaa acaaaagcta ctgtctaaca aaatgaaggg ataaataaac agatctcaac       2340
aagaaaacaa agatactttt ctacttccaa gctgcgatct ttaggctgat taaatgaaac       2400
cgataaaaaa aatactttaa agaaaagtac acaattgatc tttaggcaga ccagttgact       2460
acttcctgta tttctaagca tatacgatcc atgctaactc actaattgaa aagaagtgag       2520
tttgttaacc ttttatgtac acagcaatca ccacacgaaa gacctcatga aaagtaggat       2580
aagtgtaagt gtaattcata ttttatccca gtgcataaat ttaaaatatc ttacttttgc       2640
gacagtaaaa aagatattgg aagttttct tatgtatgta aaattaaatt aagcccatct       2700
atatatcatt gcagggtctc tgacacctgc aatctcctta tgattcgcat atttcagtga       2760
ccatttgccg attccatctc agatatcttt ctcatcaatg gaggcgggta tagtaccaga       2820
cagcacggtg atagatatgc caaattccag aatcctgaca cctgctggag caatcaatct       2880
cttctcaggt ccctcgcttc agatgtccct tcacttcagc tccatggaca gggaggccag       2940
ggtgctcagg tacagggaga agaagaaggc caggaagttt gagaagacaa tacgttatga       3000
aacaagaaag gcgtatgcag aggcacgacc ccggatcaag ggccgtttcg ccaagagatc       3060
agatgtgcag atcgaagtgg accagatgtt ctccactgca gctctatctg acggtagcta       3120
tggtactgtt ccatggttct gatgggactc atgagacgct atcttatagg catatatatg       3180
gggacttact gagtagcaat aacatcgatc cagtgggagt agttctagac aatctgtgtt       3240
atgaataata gtgtgttgtt tgcgacttaa aattgatcaa gtaccttagc tttttaaagt       3300
tttgctttgt aatttccgga tagcagatat atattgttgg tacttgctca gtagctttaa       3360 gttttttgaag taagcaaaga gcagtgatga gatgaaatga gtatgtgtat aactgtatat       3420
agataattct agggtaccct ggccaacaat cacagtagca acaatgcttt aggggtttag       3480
gtgacgaatt gggggtttag ttgtttacta tgaagtagca ccaaaatggt ggaacatata       3540
tattcctatt ttcgttccat catgacatat aactgctgtc taaccagcct atgttgactg       3600
aaaacaaagc tcgtttcatt acaaaataaa agatggaacc ctgattaagt gtgtccactg       3660
gccagatagt atcatagtag tataataatg aactggagtt caagtctttt atattccact       3720
tggatctcgg tgccattttc ttaatgatgt atcttagtga tgggctatca ttgtatccgg       3780
ttggaatttc agcagaggtg aaggtgatgg tgttcactca gcttttaaat atccattatt       3840
cttacagccc tccagatcat tctggatgaa aagaaaagca gtgacaaaga atttactgtt       3900
gctttaacca tgagaatcat atcttccag cacggcctat cttctcacta aaccatgagc       3960
tatcggtgat cagtaactcg aatgatagtt gtagggaata taggaacatt gcctgatact       4020
gataggtaca ccattgtggt tgggtgatat aagtacaaca aactcacaga aaagtttccc       4080
tattattttg tgaatcaaga gagcataaat aaggaagctc tttctcattc tcagtgcatt       4140
cctcttccct ttcactagca actagtggca tggatcttat tgccttttgt tttgagatgg       4200
agcattcacc aaatatctaa ggcatctcag ggcaccaacc gcatatacag gaatacagga       4260
tacatctaat cgttttttggc taagcttgac tgtatcggtt agatattgca caaaaaacag       4320
agttaggaat taagccctaa gagatggtaa ttggaaactg gaaagtgaac ttttcatttc       4380
aaatatcaac aaagagaggt caaaaaagta aagtgaaata aagcacacgg gagatacaga       4440
tccatatttt gaccgaaact gacgacatat accactctag tatggataga gagaacaaat       4500
```

-continued

| | |
|---|---|
| caaagttctg cagaagataa aactagacat agttgactag taacagaaga gattcctgaa | 4560 |
| cttctcact gaaactatca agcaaataga taaaactcgt ggtgatattt catccacatc | 4620 |
| agcactgaga acagaacagc aagcaagcag tttgattgtg atggagggag ctcctagcac | 4680 |
| atcatcatat tatgaagtaa tatttaataa tcatggaagt atgatgaagg tattttctg | 4740 |
| gcaacagttc ttgtttgatg catcagaata cctgattaac gtggaattaa tcaagcatca | 4800 |
| gaatcca | 4807 |

<210> SEQ ID NO 21
<211> LENGTH: 5283
<212> TYPE: DNA
<213> ORGANISM: Oryza sativa

<400> SEQUENCE: 21

| | |
|---|---|
| aaagcaaaga tgaacagagg tggactgttc tccttacaaa tttattgcaa aaaaaaaagt | 60 |
| agattctcta tggagaggca tatttaacgt tatagcaggg ctataataag aaacagatgg | 120 |
| ctcaaagaaa atgataagca acaaataacc cataaaggac ccatgtcata tatagatagg | 180 |
| ccttgcaaac aaacaaaaaa aaggtatgca aggaaataat agttccttca gcagttgaga | 240 |
| aatcatataa cagaagaaaa aaaacacatt ggtaataatt tgacttctcc actagaatag | 300 |
| atattttgg atgagggagg ccggcaaaga aactatttag tgacatggca ggccgctttg | 360 |
| gaacttttct catgtatctg cactggctac ctcacaccgg aggttcgtaa aggcggaacg | 420 |
| gctaaggggg agtgccaatg actggcacaa aaccgcatgc tttggaatcc cagagaaccc | 480 |
| aaccctccct ttctcttttg caaagaatg tgcataaaga gagagaggca gcatctttcc | 540 |
| tctgctcttt tttgttttc cctttatttg tacatcatca cagtggcttc caattctccc | 600 |
| cctttgggct tagttccatc taagagatgt ccattgaatt gtttagggac aatcctagga | 660 |
| atgcatatgg gaggattcta ttgatccctg taaaatctct ttagggacag tcctaagtta | 720 |
| aaatggaaca tgattacgac aaaagagaat cagtgtactc atcactaaaa tgcaaagctt | 780 |
| ttttgcgcaa aagcgcgatt gctttggctt aaaaggtatt gacatcagtt caggttagat | 840 |
| acttagattt agctcaaggg cgccaattct ccataggacc cgccaaagtg cacaaaatct | 900 |
| ttatctgaaa acgaccctc cattgaggat tggcatcagg gggtgagaag agaaacgctg | 960 |
| aagcagcaaa catccaaagg caaccacaag acaggcattg cagccgccgc tcgcccccccc | 1020 |
| cccccccccc cccggggatc gcgccaagtg tcaatcgctg gattcgactt gacaccccct | 1080 |
| tactattagt atactctaca ctcaaactcc ccaggacaaa aacaccgtga ctttcccctc | 1140 |
| cctagctcct tccaaaaaac actcacaaaa ttccacaaga gccatgcgag gtagaggaac | 1200 |
| aggagaagac gcatacacac acgacacata gagagagagg acaaacacaa tagcttggat | 1260 |
| cgatagactt gtccatgtgg tgcaagctaa agctactact accacaagca aggctacttc | 1320 |
| gttcatgaat tataattttg gtggcaacgt gttcgaccag gaggttggag ttggaggcga | 1380 |
| aggaggagga ggaggagagg ggagcggctg cccatgggcg cggccgtgcg acgggtgccg | 1440 |
| cgcggcgccg agcgtggtgt actgccgcgc ggacgcggcg tacctgtgcg cgtcgtgcga | 1500 |
| cgcgcgggtg cacgcggcca accgcgtggc gtcccgccac gagcgcgtgc gggtgtgcga | 1560 |
| ggcctgcgag cgcgccccgg ccgcgctcgc gtgccgcgcc gacgccgccg cgctgtgcgt | 1620 |
| ggcgtgcgac gtgcaggtgt actccgcgaa cccgctcgcc aggcgccacc agcgcgtccc | 1680 |
| cgtcgcgccg ctcccggcca tcaccatccc ggccacctcc gtcctcgctg aggcggtggt | 1740 |

-continued

| | |
|---|---|
| ggccaccgcc accgtcctcg gcgacaagga cgaggaggtg gactcttggc ttctcctctc | 1800 |
| caaagattcc gacaacaaca acaacaataa caacaacaac gacaacgaca ataacgacaa | 1860 |
| caacaacagc aacagcagca acaacggcat gtattttggt gaagtcgatg agtactttga | 1920 |
| tcttgtcggg tacaattcgt actacgacaa ccgcatcgaa acaaccaag atcggcagta | 1980 |
| tgggatgcat gaacagcaag agcagcagca gcagcagcag gagatgcaaa aggagtttgc | 2040 |
| agagaaggaa gggagcgagt gtgtggtacc ttcacagatc acaatgctga gtgagcagca | 2100 |
| gcatagtggt tatggagttg tgggagcaga ccaggccgcc tccatgaccg ccggcgtcag | 2160 |
| tgcttacaca gattccatca gcaacagcgt gagttcatct attactagct gcaactattt | 2220 |
| tttttttcaga gaatgaacat ctattactgt tgttagttag ttgttactac atgccacgtt | 2280 |
| gtcaatgttt tagagttcat actagtactt ttgagtggaa aaacattctc caaacaaaag | 2340 |
| ctactgtcta acaaaatgaa gggataaata aacagatctc aacaagaaaa caaagatact | 2400 |
| tttctacttc caagctgcga tctttaggct gattaaatgg aaccgataaa aaaatactt | 2460 |
| taaagaaaag tacacaattg atcttaggc agaccagttg actacttcct gtatttctaa | 2520 |
| gcatatacga tccatgctaa ctcactaatt gaaagaagt gagtttgtta acctttatg | 2580 |
| tacacagcaa tcaccacacg aaagacctca tgaaaagtag gataagtgta agtgtaattc | 2640 |
| atattttatc ccagtgcata aatttaaaat atcttacttt tgcgacagta aaaaagatat | 2700 |
| tggaagtttt tcttatgtat gtaaaattaa attaagccca tctatatatc attgcagggt | 2760 |
| ctctgacacc tgcaatctcc ttaggccagt cacaatgggg gtttcactgg tgtgtcatgc | 2820 |
| acatttaata ggggtaagac tgaataaaaa atgattattt gcatgaaatg gggatgagag | 2880 |
| agaaggaaag agtttcatcc tggtgaaact cgtcagcgtc gtttccaagt cctcggtaac | 2940 |
| agagtgaaac ccccgttgag gccgattcgt ttcattcacc ggatctcttg cgtccgcctc | 3000 |
| cgccgtgcga cctccgcatt ctcccgcgcc gcgccggatt ttgggtacaa atgatcccag | 3060 |
| caacttgtat caattaaatg ctttgcttag tcttggaaac gtcaaagtga aaccccctcca | 3120 |
| ctgtggggat tgtttcataa aagatttcat ttgagagaag atggtataat attttgggta | 3180 |
| gccgtgcaat gacactagcc attgtgactg gccttatgat tcgcatattt cagtgaccat | 3240 |
| ttgccgattc catctcagat atctttctca tcaatggagg cgggtatagt accagacagc | 3300 |
| acggtgatag atatgccaaa ttccagaatc ctgacacctg ctggagcaat caatctcttc | 3360 |
| tcaggtccct cgcttcagat gtcccttcac ttcagctcca tggacaggga ggccagggtg | 3420 |
| ctcaggtaca gggagaagaa gaaggccagg aagtttgaga agacaatacg ttatgaaaca | 3480 |
| agaaaggcgt atgcagaggc acgacccccgg atcaagggcc gtttcgccaa gagatcagat | 3540 |
| gtgcagatcg aagtggacca gatgttctcc actgcagctc tatctgacgg tagctatggt | 3600 |
| actgttccat ggttctgatg ggactcatga gacgctatct tataggcata tatatgggga | 3660 |
| cttactgagt agcaataaca tcgatccagt gggagtagtt ctagacaatc tgtgttatga | 3720 |
| ataatagtgt gttgtttgcg acttaaaatt gatcaagtac cttagctttt taaagttttg | 3780 |
| cttttgtaatt tccggatagc agatatatat tgttggtact tgctcagtag ctttaagttt | 3840 |
| ttgaagtaag caaagagcag tgatgagatg aaatgagtat gtgtataact gtatatagat | 3900 |
| aattctaggt taccttggcc aacaatcaca gtagcaacaa tgctttaggg gtttaggtga | 3960 |
| cgaattgggg gtttagttgt ttactatgaa gtagcaccaa aatggtggaa catatatatt | 4020 |
| cctatttttcg ttccatcatg acatataact gctgtctaac cagcctatgt tgactgaaaa | 4080 |
| caaagctcgt ttcattacaa aataaaagat ggaaccctga ttaagtgtgt ccactggcca | 4140 |

```
gatagtatca tagtagtata ataatgaact ggagttcaag tcttttatat tccacttgga    4200
tctcggtgcc attttcttaa tgatgtatct tagtgatggg ctatcattgt atccggttgg    4260
aatttcagca gaggtgaagg tgatggtgtt cactcagctt ttaaatatcc attattctta    4320
cagccctcca gatcattctg gatgaaaaga aaagcagtga caaagaattt actgttgctt    4380
taaccatgag aatcatatct ttccagcacg gcctatcttc tcactaaacc atgagctatc    4440
ggtgatcagt aactcgaatg atagttgtag ggaatatagg aacattgcct gatactgata    4500
ggtacaccat tgtggttggg tgatataagt acaacaaact cacagaaaag tttccctatt    4560
attttgtgaa tcaagagagc ataaataagg aagctctttc tcattctcag tgcattcctc    4620
ttccctttca ctagcaacta gtggcatgga tcttattgcc ttttgttttg agatggagca    4680
ttaccaaaat atctaaggca tctcagggca ccaaccgcat atacaggaat acaggataca    4740
tctaatcgtt tttggctaag cttgactgta tcggttagat attgcacaaa aaacagagtt    4800
aggaattaag ccctaagaga tggtaattgg aaactggaaa gtgaactttt catttcaaat    4860
atcaacaaag agaggtcaaa aaagtaaagt gaaataaagc acacgggaga tacagatcca    4920
tattttgacc gaaactgacg acatatacca ctctagtatg gatagagaga acaaatcaaa    4980
gttctgcaga agataaaaact agacatagtt gactagtaac agaagagatt cctgaacttt    5040
ctcactgaaa ctatcaagca aatagataaa actcgtggtg atatttcatc cacatcagca    5100
ctgagaacag aacagcaagc aagcagtttg attgtgatgg agggagctcc tagcacatca    5160
tcatattatg aagtaatatt taataatcat ggaagtatga tgaaggtatt tttctggcaa    5220
cagttcttgt ttgatgcatc agaatacctg attaacgtgg aattaatcaa gcatcagaat    5280
cca                                                                 5283
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 22
ttctcctctc caaagattcc                                                 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 23
catacgcctt tcttgtttca                                                 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

```
<400> SEQUENCE: 24
tccatcttgg catctctcag                                            20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 25
gtacccgcat caggcatctg                                            20
```